US007375206B2

(12) United States Patent
Lobanenkov et al.

(10) Patent No.: US 7,375,206 B2
(45) Date of Patent: May 20, 2008

(54) BROTHER OF THE REGULATOR OF IMPRINTED SITES (BORIS)

(75) Inventors: Victor V. Lobanenkov, Rockville, MD (US); Dmitri I. Loukinov, Germantown, MD (US); Herbert C. Morse, III, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 334 days.

(21) Appl. No.: 10/505,377

(22) PCT Filed: Feb. 21, 2003

(86) PCT No.: PCT/US03/05186

§ 371 (c)(1),
(2), (4) Date: Oct. 20, 2004

(87) PCT Pub. No.: WO03/072799

PCT Pub. Date: Sep. 4, 2003

(65) Prior Publication Data

US 2005/0182249 A1    Aug. 18, 2005

Related U.S. Application Data

(60) Provisional application No. 60/358,889, filed on Feb. 22, 2002.

(51) Int. Cl.
*C07H 21/04* (2006.01)
*C07H 21/02* (2006.01)
*C12Q 1/68* (2006.01)

(52) U.S. Cl. .................... 536/23.5; 536/23.1; 435/6
(58) Field of Classification Search ............... None
See application file for complete search history.

(56) References Cited

U.S. PATENT DOCUMENTS

| 5,279,721 A | 1/1994 | Schmid |
| 5,801,030 A | 9/1998 | McVey et al. |
| 5,837,511 A | 11/1998 | Falck-Pedersen et al. |
| 5,849,561 A | 12/1998 | Falck-Pedersen |
| 5,972,643 A | 10/1999 | Lobanenkov et al. |

FOREIGN PATENT DOCUMENTS

| WO | WO 97/12986 A2 | 4/1997 |
| WO | WO 98/53087 A1 | 11/1998 |
| WO | WO02074913 A2 * | 9/2002 |

OTHER PUBLICATIONS

Skolnick, J. and Fetrow, J.S. From genes to protein structure and function: novel applications of computational approaches in the genomic era. 2000. Trends in Biotechnology. vol. 18 No. 1, pp. 34-39.*
Burgess, Shaheen, Ravera, Jaye, Donahue, and Winkles Possible dissociation of the heparin-binding and mitogenic activities of heparin-binding (acidic fibroblast) growth factor-1 from its receptor-binding activites by site-directed mutagenesis of a single lysine residue. 1990. Journal of Cell Biology, vol. 111, pp. 2129-2138.*
Lazar, E., Watanabe, S., Dalton, S., andd Sporn, M.B. Transforming growth factor a: mutation of aspartic acid 47 and leucine 48 results in different biological activities. 1988. Molecular and Cellular Biology, vol. 8 No. 3, pp. 1247-1252.*
Schwartz, G.P., Burke, G.T., and Katsoyannis, P.G. A superactive insulin: [B10-aspartic acid] insulin (human). 1987. Proceedings of the National Academy of Sciences, vol. 84, pp. 6408-6411.*
Lin, M.C., Wright, D.E., Hruby, V.J., and Rodbell, M. Structure-function relationships in glucagon: properties of highly purified Des-His1-, Monoiodo-, and [Des-Asn28, Thr29](homoserine lactone27)-glucagon. 1975. Biochemistry, vol. 14, pp. 1559-1563.*
Freshney, R.I. Culture of Animal Cells, Alan R. Liss, Inc. 1983. New York. p. 4.*
Dermer, G.B. Another anniversary for the war on cancer. 1994. Biotechnology, vol. 12, p. 320.*
Galcheva-Gargova, Z., Konstantinov, K.N., Wu, I., Klier, F.G., Barrett, T., and Davis, R.J. Binding of zinc finger protein ZPR1 to the epidermal growth factor receptor. 1996. Science, vol. 272, pp. 1797-1802.*
Klenova et al., *Seminars in Cancer Biology*, 12, 399-414 (2002).
Loukinov et al.,*PNAS*, 99(10), 6806-6811, (May 14, 2002).
D'Arcy et al., "The Potential of BORIS Detected in the Leukocytes of Breast Cancer Patients as an Early Marker of Tumorigenesis," *Clin. Cancer Res.*, 12(20), pp. 5978-5986, (Oct. 15, 2006).
Risinger et al., "Global Expression Analysis of Cancer/Testis Genes in Uterine Cancers Reveals a High Incidence of BORIS Expression," *Clin. Cancer Res.*, 13 (6), pp. 1713-1719, (Mar. 15, 2007).

(Continued)

*Primary Examiner*—Larry R. Helms
*Assistant Examiner*—Anne M. Gussow
(74) *Attorney, Agent, or Firm*—Leydig, Voit & Mayer, Ltd.

(57) ABSTRACT

An isolated or purified nucleic acid molecule consisting essentially of a nucleotide sequence encoding a human or a non-human BORIS, or a fragment of either of the foregoing; an isolated or purified nucleic acid molecule consisting essentially of a nucleotide sequence that is complementary to a nucleotide sequence encoding a human or a non-human BORIS, or a fragment of either of the foregoing; a vector comprising such an isolated or purified nucleic acid molecule; a cell comprising such a vector; an isolated or purified polypeptide molecule consisting essentially of an amino acid sequence encoding a human or a non-human BORIS, or a fragment of either of the foregoing; a cell line that produces a monoclonal antibody that is specific for an aforementioned isolated or purified polypeptide molecule; and the monoclonal antibody produced by the cell line; methods of diagnosing a cancer or a predisposition to a cancer in a male or female mammal; a method of prognosticating a cancer in a mammal; a method of assessing the effectiveness of treatment of a cancer in a mammal; a method of treating a mammal prophylactically or therapeutically for a cancer, and a composition comprising a carrier and an inhibitor of BORIS.

21 Claims, 12 Drawing Sheets

OTHER PUBLICATIONS

Adair et al., *Proc. Natl. Acad. Sci. USA*, 86, 4574-4578 (Jun. 1989).
Arnold et al., *Gene*, 253, 209-214 (2000).
Awad et al., *J. Biol. Chem.*, 274 (38), 27092-27098 (1999).
Bell et al., *Cell*, 98, 387-396 (Aug. 6, 1999).
Bell et al., *Nature*, 405, 482-485 (May 25, 2000).
Bird, *Nature*, 321, 209-213 (May 15, 1986).
Capecchi, *Science*, 244, 1288-1292 (Jun. 1989).
Chernukhin et al., *J. Biol. Chem.*, 275 (38), 29915-29921 (Sep. 22, 2000).
Feinberg, *PNAS*, 98 (2), 392-394 (Jan. 16, 2001).
Filippova et al., *Mol. Cell. Biol.*, 16 (6), 2802-2813 (Jun. 1996).
Filippova et al., *Nature Genetics*, 28, 335-343 (Aug. 2001).
Filippova et al., *Cancer Research*, 62 (1), 48-52 (2002).
GenBank accession # AF313621, Moore et al. (2002).
Hark et al., *Nature*, 405, 486-489 (May 25, 2000).
Johnson et al., *Science*, 245, 1234-1236 (Sep. 15, 1989).
Kanduri et al., *Current Biology*, 10 (14), 853-856 (2000).
Klenova et al., *Mol. Cell Biol.*, 13 (12), 7612-7624 (Dec. 1993).
Klenova et al., *J. Biol. Chem.*, 273 (41), 26571-26579 (Oct. 9, 1998).
Klenova et al., *Mol. Cell. Biol.*, 21 (6), 2221-2234 (Mar. 2001).
Kostic et al., *Oncogene*, 19, 3978-3987 (2000).
Lichtsteiner et al., *Cell*, 51, 963-973 (Dec. 24, 1987).
Lobanenkov et al., *Oncogene*, 5, 1743-1753 (1990).
Lutz et al., *Biochem. Soc. Trans.*, 28 (4), 386-390 (2000).
Lutz et al., *Nuc. Acids Res.*, 28 (8), 1707-1713 (2000).
Mansour et al., *Nature*, 336, 348-352 (Nov. 1988).
Nakagawa et al., *PNAS*, 98 (2), 591-596 (Jan. 16, 2001).
Ohlsson et al., *Trends in Genetics*, 17 (9), 520-527 (Sep. 2001).
Pack et al., *Cancer Res.*, 59, 5560-5564 (Nov. 1, 1999).
Quitschke et al., *Nuc. Acids Res.*, 28 (17), 3370-3378 (2000).
Rasko et al., *Cancer Res.*, 61, 6002-6007 (Aug. 15, 2001).
Reik et al., *Nature*, 405, 408-409 (May 25, 2000).
Saitoh et al., *EMBO J.*, 19 (10), 2315-2322 (2000).
Szabo et al., *Curr. Biol.*, 10 (10), 607-610 (May 2000).
Thorvaldsen et al., *Science*, 288, 2145-2146 (Jun. 23, 2000).
Vostrov et al., *J. Biol. Chem.*, 277 (2), 1619-1627 (Jan. 11, 2002).
Wolffe, *Curr. Biol.*, 10 (11), R463-R465 (2000).
Wylie et al., *Genome Res.*, 10 (11), 1711-1718 (2000).
Yang et al., *J. Neurochem.*, 73 (6), 2286-2298 (Dec. 1999).
Zijlstra et al., *Nature*, 342, 435-438 (Nov. 1989).

* cited by examiner

Fig. 1A

```
ACCCTCCACTCTCGCGCCAGCCCGGCGGCGGCCGGCTGTGGGCTGCAGCACGCGGTGCAC    60
GAGGCAGAGCCACAAGCCAAAGACGGAGTGGGCCGAGCATTCCGGCCACGCCTTCCGCGG   120
CCAAGTCATTATGGCAGCCACTGAGATCTCTGTCCTTTCTGAGCAATTCACCAAGATCAA   180
AGAACTCGAGTTGATGCCGGAAAAAGGCCTGAAGGAGGAGGAAAAAGACGGAGTGTGCAG   240
AGAGAAAGACCATCGGAGCCCTAGTGAGTTGGAGGCCGAGCGTACCTCTGGGGCCTTCCA   300
GGACAGCGTCCTGGAGGAAGAAGTGGAGCTGGTGCTGGCCCCCTCGGAGGAGAGCGAGAA   360
GTACATCCTGACCCTGCAGACGGTGCACTTCACTTCTGAAGCTGTGGAGTTGCAGGATAT   420
GAGCTTGCTGAGCATACAGCAGCAAGAAGGGGTGCAGGTGGTGGTGCAACAGCCTGGCCC   480
TGGGTTGCTGTGGCTTGAGGAAGGGCCCCGGCAGAGCCTGCAGCAGTGTGTGGCCATTAG   540
TATCCAGCAAGAGCTGTACTCCCCGCAAGAGATGGAGGTGTTGCAGTTCCACGCTCTAGA   600
GGAGAATGTGATGGTGGCCAGTGAAGACAGTAAGTTAGCGGTGAGCCTGGCTGAAACTGC   660
TGGACTGATCAAGCTCGAGGAAGAGCAGGAGAAGAACCAGTTATTGGCTGAAAGAACAAA   720
GGAGCAGCTCTTTTTTGTGGAAACAATGTCAGGAGATGAAAGAAGTGACGAAATTGTTCT   780
CACAGTTTCAAATTCAAATGTGGAAGAACAAGAGGATCAACCTACAGCTGGTCAAGCAGA   840
TGCTGAAAAGGCCAAATCTACAAAAAATCAAAGAAAGACAAAGGGAGCAAAAGGAACCTT   900
CCACTGTGATGTCTGCATGTTCACCTCTTCTAGAATGTCAAGTTTTAATCGTCATATGAA   960
AACTCACACCAGTGAGAAGCCTCACCTGTGTCACCTCTGCCTGAAAACCTTCCGTACGGT  1020
CACTCTGCTGCGGAACCATGTTAACACCCACACAGGAACCAGGCCCTACAAGTGTAACGA  1080
CTGCAACATGGCATTTGTCACCAGTGGAGAACTCGTCCGACACAGGCGCTATAAACATAC  1140
TCATGAGAAACCCTTTAAATGTTCCATGTGCAAGTATGCCAGTGTGGAGGCAAGTAAATT  1200
GAAGCGCCATGTCCGATCCCACACTGGGGAGCGCCCCTTTCAGTGTTGCCAGTGCAGCTA  1260
TGCCAGCAGAGATACCTACAAGCTGAAACGCCACATGAGAACGCACTCAGGTGAGAAGCC  1320
TTACGAATGCCACATCTGCCACACCCGCTTCACCCAGAGCGGGACCATGAAAATACATAT  1380
TCTGCAGAAACACGGCGAAAATGTCCCCAAATACCAGTGTCCCCATTGTGCCACCATCAT  1440
TGCACGGAAAAGCGACCTACGTGTGCATATGCGCAACTTGCATGCTTACAGCGCTGCAGA  1500
GCTGAAATGCCGCTACTGTTCTGCTGTCTTCCATGAACGCTATGCCCTCATTCAGCACCA  1560
GAAAACTCATAAGAATGAGAAGAGGTTCAAGTGCAAACACTGCAGTTATGCCTGCAAGCA  1620
GGAACGTCATATGACCGCTCACATTCGTACCCACACTGGAGAGAAACCATTCACCTGCCT  1680
TTCTTGCAATAAATGTTTCCGACAGAAGCAACTTCTAAACGCTCACTTCAGGAAATACCA  1740
CGATGCAAATTTCATCCCGACTGTTTACAAATGCTCCAAGTGTGGCAAAGGCTTTTCCCG  1800
CTGGATTAACCTGCACAGACATTCGGAGAAGTGTGGATCAGGGGAAGCAAAGTCGGCTGC  1860
TTCAGGAAAGGGAAGAAGAACAAGAAAGAGGAAGCAGACCATCCTGAAGGAAGCCACAAA  1920
GGGTCAGAAGGAAGCTGCGAAGGGATGGAAGGAAGCCGCGAACGGAGACGAAGCTGCTGC  1980
TGAGGAGGCTTCCACCACGAAGGGAGAACAGTTCCCAGGAGAGATGTTTCCTGTCGCCTG  2040
CAGAGAAACCACAGCCAGAGTCAAAGAGGAAGTGGATGAAGGCGTGACCTGTGAAATGCT  2100
CCTCAACACGATGGATAAGTGAGAGGGATTCGGGTTGCGTGTTCACTGCCCCCAATTCCT  2160
AAAGCAAGTTAGAAGTTTTTAGCATTTAAGGTGTGAAATGCTCCTCAACACGATGGATAA  2220
GTGAGAGAGAGTCAGGTTGCATGTTCACTGCCCCTAATTCCTAAAGCAAGTTAGAAATTT  2280
TTAGCATTTTCTTTGAAACAATTAAGTTCATGACAATGGATGACACAAGTTTGAGGTAGT  2340
GTCTAGAATTGTTCTCCTGTTTGTAGCTGGATATTTCAAAGAAACATTGCAGGTATTTA  2400
TAAAAGTTTTAAACCTTGAATGAGAGGGTAACACCTCAAACCTATGGATTCATTCACTTG  2460
ATATTGGCAAGGTGGCCCACAATGAGTGAGTAGTGATTTTGGATATTTCAAAATAGTCT  2520
AGACCAGCTAGTGCTTCCACAGTCAAAGCTGGACATTTTTATGTTGCATTATATACACCC  2580
ATGATATTTCTAATAATATATGGTTTTAAACATTAAAGACAAATGTTTTTATACAAATGA  2640
ATTTTCTACAAAATTTAAAGCTACCATAATGCTTTTAATTAGTTCTAAATTCAACCAAAA  2700
AATGTTTTACTCTTATAAAAAGGAAAACTGAGTAGGAAATGAAATACTAGATTAGACTAG  2760
AAAATAAGGAATAAATCGATTTTACTTTGGTATAGGAGCAAGGTTCACCTTTAGATTTTT  2820
GTATTCTCTTTTAATTATGCTCCTTGGCAGGTATGAAATTGCCCTGGTTACATTCCATTA  2880
TTGCTTATTAGTATTTCACTCCATAACCCTTTTTCTGCTAAAACTACTCTTTTTATATT  2940
TGTAAAATAATTGGCAGAGTGAGAAGAAACATAAAATCAGATAAGGCAAATGTGTACCTG  3000
TAAGGAATTTGTACTTTTTCATAATGCCCAGTGATTAGTGAGTATTTCCCTTTTGCCAGT  3060
TGACAAGATTTTTCCACCCTCGAGCAGCGTGAGAGATGCCTCTTTAACACTTGAAATTCA  3120
TTTCTATCTGGATACAGAGGCAGATTTTCTTCATTGCTTAGTTGAGCAGTTTGTTTTGC  3180
TGCCAACCTGTCTCCACCCCTGTATTTCAAGATCATTGATAAGCCCTAAATTCAAATTCT  3260
TAAGATATGGACCTTTTATTGAAAATATCACAAGTTCAGAATCCCTATACAATGTGAATA  3300
TGTGGAAATAATTTCCCAGCAGGAAGAGCATTATATTCTCTTTGTACCAGCAAATTAATT  3360
TAACTCAACTCACATGAGATTTAAATTCTGTGGGCTGTAGTATGCCATCATTGTGACTGA  3420
ATTTGTGCAATGGTTTCTTAATTTTTTTACTGTTATTTAAAGATGTTTTACATAATTCAA  3480
TAAAATGAAATGACTTAAAATTGCAAAAAAAAAAAAAAAAAAAAAAAAAAAAAAAAAAA  3540
A      (SEQ ID NO:1)                                         3541
```

Fig. 1B

```
CCATTTTGTGCACCTTGATCAAAGCCCATGTCTACTAGGCCCCAGCACCTCTGCACCCCA      60
TAAAGATTGCACGCTCTTTTTCCATCAGGGGTCGTCACCATGGCTGCCGCTGAGGTCCCT     120
GTCCCTTCTGGGTACTTCACCCAGATCAAAGAGCAGAAGTTGAAGCCTGGAGACCTAGAG     180
GAGGAGAAAGAGGAGGACGGGGTACAAAGAGTGGAAGCCCAGGAGGGAGTTGTCAAGGAG     240
GTGGAGGCCGAGAACAGTTGCCTGCTTCTGGAGGCCAGGGCCCCGGTGGAGAGCGACAGG     300
CGGATCCTGACCCTGCAAACGGTGCACCTGGAGTCCCAGGATGTGCACCTACAGGGGCTG     360
GGATGGCTGAGCGTGCCACACTCTGAGGAGCTTTCAGGGACGGTACCAGAGGCGGAAGGC     420
ATACTGCAGTTGCCATCCGTGCTGTGGCTCGACCCAGAGCCCCAGCTCAGCCTTCAGCAT     480
TGCGTGACGGTCAGCATCCCGGAAGAGCTGTACCCACCAGAGGAGCTGCAGCGGATACAT     540
TTTCACCTGCTGAGAGAGAATGTGCTAATGGCCGAGGAGAACCCAGAGTTAACACCAGAC     600
TTGGACGAAAGCACAGCCCTGAAAAAGCCCGAAGAAGATGAAAAGGACCAGCTCCCGCCC     660
CAGGGAGAGACAGACAAGAGAGAAGAGAGGTTGCTCCTTCTGGAAATGAAACCAAAAGAG     720
GGAAAAGACGACGAAATTGTCCTGACCATTTCCCATCTAAGCCTCGAAGAACAGCAAGAT     780
CCACCAGCGGCCAATCAGACAAGTGTGCCGGGAGCCAAAGCCGCAAAACCAAACGGCGG     840
AGGCAGACCAAGGGAAAGCCTCAGAGCTTTCAGTGTGACACCTGCCCGTTCACTTCCTCC     900
AAGCTCTCAACTTTCAATCGTCACATCAAAATTCACAGCAATGAGAGGCCACACCTGTGT     960
CACCTGTGCCTGAAGGCCTTCCGGACTGTCACTCTTCTTAGGAACCATGTGAACACCCAC    1020
ACAGGAACCAGGCCCCACAAGTGCAGGGACTGCGACATGGCGTTTGTCACCAGCGGAGAA    1080
CTCGTCCGGCACAGGCGTTACAAACACACTTATGAGAAGCCCTTCAAGTGCTCCCTGTGC    1140
AAGTACGCCAGCGTCGAGGCAAGCAAGATGAAGCGTCACATCCGCTCACACACGGGTGAG    1200
CGTCCCTTCCAGTGTTGCCAGTGTGCTTATGCCAGCAGGGACTCCTACAAGCTGAAGCGC    1260
CACATGAGGACACACTCAGGTGAGAAGCCGTATGAATGTCCCACCTGTCACGTCCGGTTC    1320
ACCCAGAGCGGGACCATGAAAATCCATATAGCACAGAAGCACGGAGAGAATGTGCCCAAA    1380
TACGAGTGTCCCCACTGTGCCACCATCATCGCGAGGAAGAGCGACCTGCGTGTCCATCTG    1440
CGTAACCTGCACAGCCAGAGCCCGGAGGAGATGAAGTGCCGATACTGTCCCGCTGGCTTC    1500
CATGAGCGCTATGCCCTCATTCAGCACCAGAGGACCCACAAGAACGAGAAGAAGTTCAAG    1560
TGCAAGCAGTGCGATTACGCGTGCAAGCAGGAGCGATGCTTGAAGGCGCACATGCGCATG    1620
CACACAGGAGAGAAGCCCTTCTCCTGCCTGGCCTGCAACAAGCACTTCCGACAGAAGCAG    1680
CTACTGACCGTGCACCTGAGGAAGTACCATGACCCGAACTTCGTCCCCAATCTGCACCTG    1740
TGCCTCAAGTGTGATAAACGTTTCTCCCGCTGGAGTAACCTGCAGAGACACAGAAAGAAG    1800
TGTGACCCGGAGCATGAGACGTTAGCCCCCAACAAGGACAGGAGACCAGTGACAAGGACA    1860
CAGGCCTCGGAGGGAGAAGCAGGACACAAGGAAGGGGAGCCTCAGTGCCCTGGGGAGCAG    1920
GCTCTGGGCCACCAAGGAGAAGCAGCGGGGAGCCAGAGCCCAGACCACGGCCTTACCTGC    1980
GAGATGATCTTTAACATGATGGATAAGTGATGGATAAGTGAGCAGTCGTGCCTCTCCGTG    2040
CAGTGGCCTCTGGGGGAAGAAACCAGTTAGAAATAAGTTCCCAGACACAGCACAGTGTTC    2100
TCAGAGTTTGAGATAGTGTGTAGAAATGTTTGAGAGAAGGGGAAAAAAACCCTGCAGCTA    2160
TTTCCAAAGACTTGAGTCAGAGCTCGAAGTGAAGGTGCACATATCTGGGCCCTAGCAGGT    2220
GCCCAGAATGAGTCAGGGACAGATTCTAGGTGATACTTATGTCCACGGGGCTCAGACCA    2280
GTTAACGCCTTGGTGGTCAGAGCAGAAAATTTTTGAGTTGTTGTACCCACCCTCAA      2337
(SEQ ID NO:3)
```

Fig. 2A

```
MAATEISVLSEQFTKIKELELMPEKGLKEEEKDGVCREKDHRSPSELEAERTSGAFQDSV      60
LEEEVELVLAPSEESEKYILTLQTVHFTSEAVELQDMSLLSIQQQEGVQVVVQQPGPGLL     120
WLEEGPRQSLQQCVAISIQQELYSPQEMEVLQFHALEENVMVASEDSKLAVSLAETAGLI     180
KLEEEQEKNQLLAERTKEQLFFVETMSGDERSDEIVLTVSNSNVEEQEDQPTAGQADAEK     240
AKSTKNQRKTKGAKGTFHCDVCMFTSSRMSSFNRHMKTHTSEKPHLCHLCLKTFRTVTLL     300
RNHVNTHTGTRPYKCNDCNMAFVTSGELVRHRRYKHTHEKPFKCSMCKYASVEASKLKRH     360
VRSHTGERPFQCCQCSYASRDTYKLKRHMRTHSGEKPYECHICHTRFTQSGTMKIHILQK     420
HGENVPKYQCPHCATIIARKSDLRVHMRNLHAYSAAELKCRYCSAVFHERYALIQHQKTH     480
KNEKRFKCKHCSYACKQERHMTAHIRTHTGEKPFTCLSCNKCFRQKQLLNAHFRKYHDAN     540
FIPTVYKCSKCGKGFSRWINLHRHSEKCGSGEAKSAASGKGRRTRKRKQTILKEATKGQK     600
EAAKGWKEAANGDEAAAEEASTTKGEQFPGEMFPVACRETTARVKEEVDEGVTCEMLLNT     660
MDK    (SEQ ID NO:2)                                             663
```

Fig. 2B

```
MAAAEVPVPSGYFTQIKEQKLKPGDLEEEKEEDGVQRVEAQEGVVKEVEAENSCLLLEAR      60
APVESDRRILTLQTVHLESQDVHLQGLGWLSVPHSEELSGTVPEAEGILQLPSVLWLDPE     120
PQLSLQHCVTVSIPEELYPPEELQRIHFHLLRENVLMAEENPELTPDLDESTALKKPEED     180
EKDQLPPQGETDKREERLLLLEMKPKEGKDDEIVLTISHLSLEEQQDPPAANQTSVPGAK     240
AAKPKRRRQTKGKPQSFQCDTCPFTSSKLSTFNRHIKIHSNERPHLCHLCLKAFRTVTLL     300
RNHVNTHTGTRPHKCRDCDMAFVTSGELVRHRRYKHTYEKPFKCSLCKYASVEASKMKRH     360
IRSHTGERPFQCCQCAYASRDSYKLKRHMRTHSGEKPYECPTCHVRFTQSGTMKIHIAQK     420
HGENVPKYECPHCATIIARKSDLRVHLRNLHSQSPEEMKCRYCPAGFHERYALIQHQRTH     480
KNEKKFKCKQCDYACKQERCLKAHMRMHTGEKPFSCLACNKHFRQKQLLTVHLRKYHDPN     540
FVPNLHLCLKCDKRFSRWSNLQRHRKKCDPEHETLAPNKDRRPVTRTQASEGEAGHKEGE     600
PQCPGEQALGHQGEAAGSQSPDHGLTCEMIFNMMDK        (SEQ ID NO:4)         636
```

Fig. 3A

```
         CAGGGTAAAGCAGGGGCCCTGCCAGGCCTCCGAGGGAGTGTGCTTGGTCTGGCCGAGGGC    60
         TGCTTGGCCAAGTCTGGGTGGGCTCGAGGCCACTAGGCCCAAAGCCTGCCTGGCTCTGAG   120
         GGTGCTAGGTCTAGAACCGTGCACGAGGGGAATGCCTGCTCGGGCCCGAACCTCGCTGGG   180
         CGCCGGGTGTGCACTGGCCCGGGGCCTGCTTGGACCTGAAACTTGCTAGGCCCAGGATAT   240
         GCACTGGCCGAGAGCCTGCTGGGCCCAAACCTTACTAGGCCCAGGATGTTCACTGACTGA   300
         ACCGGCTCAGGCCTAACCTTGCTAGGCCCAGGATATGCACTGGGCCAGAGTGTGCTCAGG   360
         CGGAACCTTGCCAGGCGCAGGATGTGTGCTGGCCCTAAGCCTGCTGAGGCCCAAACCTGT   420
         TCGTTCTAGGGTTTTGTACAAAATCCTGCTTTAGCCTAAATCCTGCTTAGCCTTGACCCC   480
         CTCCTAGACCCAAGCCAGATCAGCATTGTTCTGACCCTACTAAGTCCAAAACCTTTTGAG   540
         GCCAGACCTTGTTTCAACTCCAAAGCCTGCTAGGTTCCAGCACCCCCCGCATCCCTCCTC   600
         ATACCACCCCCTTCTCCCCCCTATGGAAACCGCTTGCTTATTTTTCAAACAGGCCAAGTC   660
         ATTatggcagccactgagatctctgtcctttctgagcaattcaccaagatcaaagaactc   720
1            M  A  A  T  E  I  S  V  L  S  E  Q  F  T  K  I  K  E  L
         gagttgatgccggaaaaaggcctgaaggaggaggaaaaagacggagtgtgcagagagaaa    780
 20       E  L  M  P  E  K  G  L  K  E  E  E  K  D  G  V  C  R  E  K
         gaccatcggagccctagtgagttggaggccgagcgtacctctggggccttccaggacagc   840
 40       D  H  R  S  P  S  E  L  E  A  E  R  T  S  G  A  F  Q  D  S
         gtcctggaggaagaagtggagctggtgctggcccctcggaggagagcgagaagtacatc   900
 60       V  L  E  E  V  E  L  V  L  A  P  S  E  E  S  E  K  Y  I
         ctgaccctgcagacggtgcacttcacttctgaagctgtggagttgcaggatatgagcttg   960
 80       L  T  L  Q  T  V  H  F  T  S  E  A  V  E  L  Q  D  M  S  L
         ctgagcatacagcagcaagaaggggtgcaggtggtggtgcaacagcctggccctgggttg  1020
100       L  S  I  Q  Q  Q  E  G  V  Q  V  V  V  Q  Q  P  G  P  G  L
         ctgtggcttgaggaagggccccggcagagcctgcagcagtgtgtggccattagtatccag  1080
120       L  W  L  E  E  G  P  R  Q  S  L  Q  Q  C  V  A  I  S  I  Q
         caagagctgtactcccgcaagagatggaggtgttgcagttccacgctctagaggagaat  1140
140       Q  E  L  Y  S  P  Q  E  M  E  V  L  Q  F  H  A  L  E  E  N
         gtgatggtggccagtgaagacagtaagttagcggtgagcctggctgaaactgctggactg  1200
160       V  M  V  A  S  E  D  S  K  L  A  V  S  L  A  E  T  A  G  L
         atcaagctcgaggaagagcaggagaagaaccagttattggctgaaagaacaaaggagcag  1260
180       I  K  L  E  E  E  Q  E  K  N  Q  L  L  A  E  R  T  K  E  Q
         ctcttttttgtggaaacaatgtcaggagatgaaagaagtgacgaaattgttctcacagtt  1320
200       L  F  F  V  E  T  M  S  G  D  E  R  S  D  E  I  V  L  T  V
         tcaaattcaaatgtggaagaacaagaggatcaacctacagctggtcaagcagatgctgaa  1380
220       S  N  S  N  V  E  E  Q  E  D  Q  P  T  A  G  Q  A  D  A  E
         aaggccaaatctacaaaaaatcaaagaaagacaaagggagcaaaaggaaccttccactgt  1440
240       K  A  K  S  T  K  N  Q  R  K  T  K  G  A  K  G  T  F  H  C
                                                                  =
         gatgtctgcatgttcacctcttctagaatgtcaagtttttaatcgtcatatgaaaactcac  1500
260       D  V  C  M  F  T  S  S  R  M  S  S  F  N  R  H  M  K  T  H
         ================ ZF1 ================
         accagtgagaagcctcacctgtgtcacctctgcctgaaaaccttccgtacggtcactctg  1560
280       T  S  E  K  P  H  L  C  H  L  C  L  K  T  F  R  T  V  T  L
                        ============== ZF2 ==========
         ctgcggaaccatgttaacacccacacaggaaccaggccctacaagtgtaacgactgcaac  1620
300       L  R  N  H  V  N  T  H  T  G  T  R  P  Y  K  C  N  D  C  N
         ===================                    ============
         atggcatttgtcaccagtggagaactcgtccgacacaggcgctataaacatactcatgag  1680
320       M  A  F  V  T  S  G  E  L  V  R  H  R  R  Y  K  H  T  H  E
         =========== ZF3 =====================
         aaaccctttaaatgttccatgtgcaagtatgccagtgtggaggcaagtaaattgaagcgc  1740
340       K  P  F  K  C  S  M  C  K  Y  A  S  V  E  A  S  K  L  K  R
                    ================ ZF4 =================
         catgtccgatcccacactggggagcgccccttcagtgttgccagtgcagctatgccagc  1800
360       H  V  R  S  H  T  G  E  R  P  F  Q  C  C  Q  C  S  Y  A  S
         ============                        ================
         agagatacctacaagctgaaacgccacatgagaacgcactcaggtgagaagccttacgaa  1860
380       R  D  T  Y  K  L  K  R  H  M  R  T  H  S  G  E  K  P  Y  E
         ============ ZF5 ======================
         tgccacatctgccacacccgcttcacccagagcgggaccatgaaaatacatattctgcag  1920
400       C  H  I  C  H  T  R  F  T  Q  S  G  T  M  K  I  H  I  L  Q
```

Fig. 3A (cont.)

```
                ================ ZF6 ===============================
           aaacacggcgaaaatgtccccaaataccagtgtccccattgtgccaccatcattgcacgg    1980
420        K  H  G  E  N  V  P  K  Y  Q  C  P  H  C  A  T  I  I  A  R
           ====                    =============================
           aaaagcgacctacgtgtgcatatgcgcaacttgcatgcttacagcgctgcagagctgaaa    2040
440        K  S  D  L  R  V  H  M  R  N  L  H  A  Y  S  A  A  E  L  K
           ===== ZF7 ==========================
           tgccgctactgttctgctgtcttccatgaacgctatgccctcattcagcaccagaaaact    2100
460        C  R  Y  C  S  A  V  F  H  E  R  Y  A  L  I  Q  H  Q  K  T
           ================ ZF8 ==============================
           cataagaatgagaagaggttcaagtgcaaacactgcagttatgcctgcaagcaggaacgt    2160
480        H  K  N  E  K  R  F  K  C  K  H  C  S  Y  A  C  K  Q  E  R
           =                  ================ ZF9 ======
           catatgaccgctcacattcgtacccacactggagagaaaccattcacctgcctttcttgc    2220
500        H  M  T  A  H  I  R  T  H  T  G  E  K  P  F  T  C  L  S  C
           ==========================            ==========
           aataaatgtttccgacagaagcaacttctaaacgctcacttcaggaaataccacgatgca    2280
520        N  K  C  F  R  Q  K  Q  L  L  N  A  H  F  R  K  Y  H  D  A
           ========== ZF10 =============================
           aatttcatcccgactgtttacaaatgctccaagtgtggcaaaggcttttcccgctggatt    2340
540        N  F  I  P  T  V  Y  K  C  S  K  C  G  K  G  F  S  R  W  I
                          =================== ZF11 =========
           aacctgcacagacattcggagaagtgtggatcaggggaagcaaagtcggctgcttcagga    2400
560        N  L  H  R  H  S  E  K  C  G  S  G  E  A  K  S  A  A  S  G
           ============================
           aagggaagaagaacaagaaagaggaagcagaccatcctgaaggaagccacaaagggtcag    2460
580        K  G  R  R  T  R  K  R  K  Q  T  I  L  K  E  A  T  K  G  Q
           aaggaagctgcgaagggatggaaggaagccgcgaacggagacgaagctgctgctgaggag    2520
600        K  E  A  A  K  G  W  K  E  A  A  N  G  D  E  A  A  E  E
           gcttccaccacgaagggagaacagttcccaggagagatgtttcctgtcgcctgcagagaa    2580
620        A  S  T  T  K  G  E  Q  F  P  G  E  M  F  P  V  A  C  R  E
           accacagccagagtcaaagaggaagtggatgaaggcgtgacctgtgaaatgctcctcaac    2640
640        T  T  A  R  V  K  E  E  V  D  E  G  V  T  C  E  M  L  L  N
           acgatggataagTGAGAGGGATTCGGGTTGCGTGTTCACTGCCCCCAATTCCTAAAGCAA    2700
660        T  M  D  K
           GTTAGAAGTTTTTAGCATTTAAGGTGTGAAATGCTCCTCAACACGATGGATAAGTGAGAG    2760
           AGAGTCAGGTTGCATGTTCACTGCCCCTAATTCCTAAAGCAAGTTAGAAATTTTTAGCAT    2820
           TTTCTTTGAAACAATTAAGTTCATGACAATGGATGACACAAGTTTGAGGTAGTGTCTAGA    2880
           ATTGTTCTCCTGTTTGTAGCTGGATATTTCAAAGAAACATTGCAGGTATTTTATAAAAGT    2940
           TTTAAACCTTGAATGAGAGGGTAACACCTCAAACCTATGGATTCATTCACTTGATATTGG    3000
           CAAGGTGGCCCACAATGAGTGAGTAGTGATTTTTGGATATTTCAAAATAGTCTAGACCAG    3060
           CTAGTGCTTCCACAGTCAAAGCTGGACATTTTTATGTTGCATTATATACACCCATGATAT    3120
           TTCTAATAATATATGGTTTTAAACATTAAAGACAAATGTTTTTATACAAATGAATTTTCT    3180
           ACAAAATTTAAAGCTACCATAATGCTTTTAATTAGTTCTAAATTCAACCAAAAAATGTTT    3240
           TACTCTTATAAAAAGGAAAACTGAGTAGGAAATGAAATACTAGATTAGACTAGAAAATAA    3300
           GGAATAAATCGATTTTACTTTGGTATAGGAGCAAGGTTCACCTTTAGATTTTGTATTCT    3360
           CTTTTAATTATGCTCCTTGGCAGGTATGAAATTGCCCTGGTTACATTCCATTATTGCTTA    3420
           TTAGTATTTCACTCCATAACCCTTTTTTCTGCTAAAACTACTCTTTTTATATTTGTAAAA    3480
           TAATTGGCAGAGTGAGAAGAAACATAAAATCAGATAAGGCAAATGTGTACCTGTAAGGAA    3540
           TTTGTACTTTTTCATAATGCCCAGTGATTAGTGAGTATTTCCCTTTTGCCAGTTGACAAG    3600
           ATTTTTCCACCCTCGAGCAGCGTGAGAGATGCCTCTTTAACACTTGAAATTCATTTCTAT    3660
           CTGGATACAGAGGCAGATTTTTCTTCATTGCTTAGTTGAGCAGTTTGTTTTGCTGCCAAC    3720
           CTGTCTCCACCCCTGTATTTCAAGATCATTGATAAGCCCTAAATTCAAATTCTTAAGATA    3780
           TGGACCTTTTATTGAAAATATCACAAGTTCAGAATCCCTATACAATGTGAATATGTGGAA    3840
           ATAATTTCCCAGCAGGAAGAGCATTATATTCTCTTTGTACCAGCAAATTAATTTAACTCA    3900
           ACTCACATGAGATTTAAATTCTGTGGGCTGTAGTATGCCATCATTGTGACTGAATTTGTG    3960
           CAATGGTTTCTTAATTTTTTTACTGTTATTTAAAGATGTTTTACATAATTCAATAAAATG    4020
           AAATGACTTAAAAATTGCAAAAAAAAAAAAAAAAAAAAAAAAAAAAAAAAAAAAAAAAAA    4080
```

Fig. 3B

```
MAATEIS-VLSEQFTKIKELELMPEKGLKEEEKDGVCREKDHRSPSELEAERTSG           54
MEGDAVEAIVEESETFIKGKERKTYQRRREGGQEEDACHLPQ--------NQTDG           47
-----AFQDSVLEE--------------EV-ELVLAPSEESE---KYILTLQTVHFT        127
GEVVQDVNSSVQMVMMEQLDPTLLQMKTEVMEGTVAPEAEAAVDDTQIITLQVVNME        104
SEAV---ELQDMSLLSIQQQEGVQVVVQQPGPGLLWLEEGPRQSLQQCVAISIQQELYSPQ    145
EQPINIGELQ---------LVQVPVPVTVP-VATTSVEE-----LQGAYENEVSKEGLAES   150
EMEVLQFHALEE--NVMVASEDSKLAVSLAETAGLIKLEEEQEKN----QLLAERTKEQLFFVE 163
--EPMICHTLPLPEGFQVVKVGANGEVETLEQGELPPQEDPSWQKDPDYQPPAKKTKKTKKSKL 212
TMSGDERSDEIVLTVSNSNVEEQEDQPTAGQADAEKA-----KSTKNQRKTKGAKGT        256
RYTEEGKD----VDVSVYDFEEEQQEGLLSEVNAEKVVGNMKPPKPTKIKKKGVKKT        265
FHCDVCMFTSSRMSSFNREMKTETSEKPHLCHLCLKTFRTVTLLRNHVNTHTGTRP         312
    ZF1    1 2 3  6                   ZF2   1 2 3  6
FQCELCSYTGPRRSNLDRHMKSHTDERPHKCHLCGRAERTVTLLRNHLNIHTGTRP         321
YKCNDCNMAFVTSGELVRHRRYKTHEKPFKCSMCKQASVEFSKLLKRHVRSHTGERP        369
    ZF3    1 2 3  6                   ZF4   1 2 3  6
HKCPDCDMAFVTSGELVRHRRVKTHEKPFKCSMCDYASVEVSKLLKRHLRSHTGERP        378
FQCCQCSYASRDTYKLKRHMRTHSGEKPYECHICHTRFTQSCTMKTHTLQKHGENVPK       427
    ZF5    1 2 3  6                   ZF6   1 2 3  6
FQCSLCSYASRDTYKLKRHMRTHSGEKPYECYTCHARFTQSCTMKMHILQKHTENVAK       436
YQCPHCATIIARKSDLRVHMRNLHAYSAAELKCRYCSAVEHERVAITQHQKTHKNEKR       485
    ZF7    1 2 3  6                   ZF8   1 2 3  6
FHCPHCDTVTARKSDLCVHLRKQHSYIEQGKKCRYCDAVEHERYALTQHQKSHKNEKR       494
FKCKHCSYACKQERHMTAHTRTHTGEKPFTCESCNKCERQKQLLNAHFRKYHDANFIPTV    545
    ZF9    1 2 3  6                   ZF10  1 2 3  6
FKCDQCDYACRQERHMIMHKRTHTGEKPYACSHCDKTFRQKQLLDMHFKRYHDPNFVPAA    554
YKCSKCCKGFSRWLNLHRHSEKCGS----GEAKSAASGKGRRTRKRKQTILKEATKGQKE    601
    ZF11   1 2 3  6
FVCSKCGKTETRRNTMARHADNCAGPDGVEGENGGETKKSKRGRKRKMRSKKEDSSDSEN    614
AAKGWKEAANGDEAAAEEASTTKGEQFPGEMFPVACRETTAR-------------         643
AEPDL--DDNEDEEEPAVEIEPEPEPQPVTPAPPPAKKRRGRPPGRTNQPKQNQP          667
-------------------------------------VKEEVDEGVTCEMLLNTMDK        663
TAIIQVEDQNTGAIENIIVEVKKEPDAEPAEGEEEEAQPAATDAPNGDLTPEMILSMMDR    727
```

Fig. 3C

```
MAAAEVPVPSGYETQIKEQKLKPGDLEEEKEEDGVQRVEAQEGVVKEVEAENSCLLEEAR      60
MAATEISVLSEQETKIKELELMPEKGLKEEEKDGVCR-EKDHRSPSEDEAERTSGAFQDS      60

----------AEV-ESDRRILTLQTVHLESQDVHLQGLGWLSVPHSEEESGTVPEAEGIL     120
VLEEVELVLAPSEESEKYILTLQTVHETSEAVELQDMSLLSIQQQEGVQ-VWVQQPG--     109

QLPSVLWLDPEPQLSLQHCVIVSIPEELVPEELQRTHFHLERENVLMAEENPETIPDED     180
--PGLLWLEEGPROSEQQCVATSIQQELYSPQEMEVLQEHALEENVMVASEDSKLAVSIA    167

ESTAE-KKPEEDEKDQLPPQGETDKREERILLLEMKPKEGKDDEIVETISHLSEEEQDP     239
ETAGLIKLEEEQEENQL----LAERTKEQDEFVETMSGDERSDEIVLTVSNSNVEEQEDQ    221
                                    ZF1
PAANQISVPGAKAAKPKRRRQIKGKPQSEQCDTCPFTSSKLSTFNRHIKIHSNERPHI      297
PTAGQADAEKAKSTKNQRK--TKGAKGIEHCDVCMFTSSRMSSFNRHMKTHISEKPHI      277
       ZF2                            ZF3
CHICLKAFRTVILERNHVNTHIGTRPHKCRDCDMAFVTSGELVRHRRYKHTYEKPFK      354
CHICLEKTERTVITLERNHVNTHIGTRPEYKCNDCNMAFVTSGELVRHRRYKHIHEKPFK     334
       ZF4                            ZF5
CSECKYASVEASKMKFHIRSHTGERPFQCCQCAVASRDSVKLKRHMRIHSGEKPYE      410
CSMCKYASVEASKIKRHVRSHTGERPFECCQCSVASRDTYKLKRHMRIHSGEKPYE      390
       ZF6                            ZF7
CPTCHVREFQSGTMKTHIIAQKHGENVPKCVECPHCATLIARKSDLRVHIERNIHSQSPEEMK    470
CHICHIRETQSGTMKIHILQKHGENVPKYQCPHCATLLARKSDLRVHMRNIHAYSAAELK     450
       ZF8                            ZF9
CRVCPAGFHERYAEIQHQRIHKNEKKEKCKQCDVAGKQERCLKAHMRMHTGEKPFS      526
CRVCSAVEHERYALIQHQKTHKNEKREKCKHCSVAGKQERHMTAHIRTHLGEKPFI      506
       ZF10                           ZF11
CLACNKHEROKQILTVHLRKYHDPNEVPNIHLCLKCDKRFSRWSNIQRHRKKCDP-      581
CLSCNKCFROKQLINAHERKYHDANEIFTVYKCSKCGKGFSRWINIHRHSEKCGSG      562

EHETLAPNKDRRPVTRTQASEGEAGHKEGEPQCP-------------------        615
EAKSAASGKGRRTRKRKQTILKEATKGQKEAAKGWKEAANGDEAAAEEASTTK        615

GEQALGHQGEAAGSQSP-------DHGLTCEMIFNMMDK                   647
GEQFPGEMFPVACREITARVKEEVDEGVTCEMLLNTMDK                   654
```

Fig. 3D

```
    CCATTTTGTGCACCTTGATCAAAGCCCATGTCTACTAGGCCCCAGCACCTCTGCACCCCA  60
    TAAAGATTGCACGCTCTTTTTCCATCAGGGGTCGTCACCatggctgccgctgaggtccct 120
  1                                           M  A  A  A  E  V  P
    gtcccttctgggtacttcacccagatcaaagagcagaagttgaagcctggagacctagag 180
  8 V  P  S  G  Y  F  T  Q  I  K  E  Q  K  L  K  P  G  D  L  E
    gaggagaaagaggaggacggggtacaaagagtggaagcccaggagggagttgtcaaggag 240
 28 E  E  K  E  E  D  G  V  Q  R  V  E  A  Q  E  G  V  V  K  E
    gtggaggccgagaacagttgcctgcttctggaggccagggcccggtggagagcgacagg  300
 48 V  E  A  E  N  S  C  L  L  L  E  A  R  A  P  V  E  S  D  R
    cggatcctgaccctgcaaacggtgcacctggagtcccaggatgtgcacctacaggggctg 360
 68 R  I  L  T  L  Q  T  V  H  L  E  S  Q  D  V  H  L  Q  G  L
    ggatggctgagcgtgccacactctgaggagctttcagggacggtaccagaggcggaaggc 420
 88 G  W  L  S  V  P  H  S  E  E  L  S  G  T  V  P  E  A  E  G
    atactgcagttgccatccgtgctgtggctcgacccagagccccagctcagccttcagcat 480
108 I  L  Q  L  P  S  V  L  W  L  D  P  E  P  Q  L  S  L  Q  H
    tgcgtgacggtcagcatcccggaagagctgtaccaccagaggagctgcagcggatacat  540
128 C  V  T  V  S  I  P  E  E  L  Y  P  P  E  E  L  Q  R  I  H
    tttcacctgctgagagagaatgtgctaatggccgaggagaacccagagttaacaccagac 600
148 F  H  L  L  R  E  N  V  L  M  A  E  E  N  P  E  L  T  P  D
    ttggacgaaagcacagccctgaaaaagcccgaagaagatgaaaaggaccagctcccgccc 660
168 L  D  E  S  T  A  L  K  K  P  E  E  D  E  K  D  Q  L  P  P
    cagggagagacagacaagagagaagagaggttgctccttctggaaatgaaaccaaaagag 720
188 Q  G  E  T  D  K  R  E  E  R  L  L  L  L  E  M  K  P  K  E
    ggaaaagacgacgaaattgtcctgaccatttcccatctaagcctcgaagaacagcaagat 780
208 G  K  D  D  E  I  V  L  T  I  S  H  L  S  L  E  E  Q  Q  D
    ccaccagcggccaatcagacaagtgtgccgggagccaaagccgcaaaaccaaaacggcgg 840
228 P  P  A  A  N  Q  T  S  V  P  G  A  K  A  A  K  P  K  R  R
    aggcagaccaagggaaagcctcagagctttcagtgtgacacctgcccgttcacttcctcc 900
248 R  Q  T  K  G  K  P  Q  S  F  Q  C  D  T  C  P  F  T  S  S
                                         ===============ZF1===
    aagctctcaactttcaatcgtcacatcaaaattcacagcaatgagaggccacacctgtgt 960
268 K  L  S  T  F  N  R  H  I  K  I  H  S  N  E  R  P  H  L  C
    ==============================                              =
    cacctgtgcctgaaggccttccggactgtcactcttcttaggaaccatgtgaacacccac 1020
288 H  L  C  L  K  A  F  R  T  V  T  L  L  R  N  H  V  N  T  H
    ================ZF2================================
    acaggaaccaggcccccacaagtgcagggactgcgacatggcgtttgtcaccagcggagaa 1080
308 T  G  T  R  P  H  K  C  R  D  C  D  M  A  F  V  T  S  G  E
                        ===================ZF3===========
    ctcgtccggcacaggcgttacaaacacacttatgagaagcccttcaagtgctccctgtgc 1140
328 L  V  R  H  R  R  Y  K  H  T  Y  E  K  P  F  K  C  S  L  C
    =====================                           ==========
    aagtacgccagcgtcgaggcaagcaagatgaagcgtcacatccgctcacacacgggtgag 1200
348 K  Y  A  S  V  E  A  S  K  M  K  R  H  I  R  S  H  T  G  E
    ==============ZF4=================================
    cgtcccttccagtgttgccagtgtgcttatgccagcagggactcctacaagctgaagcgc 1260
368 R  P  F  Q  C  C  Q  C  A  Y  A  S  R  D  S  Y  K  L  K  R
                  ===================ZF5=====================
    cacatgaggacacactcaggtgagaagccgtatgaatgtcccacctgtcacgtccggttc 1320
388 H  M  R  T  H  S  G  E  K  P  Y  E  C  P  T  C  H  V  R  F
    ============                     =====================
    acccagagcgggaccatgaaaatccatatagcacagaagcacggagagaatgtgcccaaa 1380
408 T  Q  S  G  T  M  K  I  H  I  A  Q  K  H  G  E  N  V  P  K
    ==============ZF6==========================
    tacgagtgtccccactgtgccaccatcatcgcgaggaagagcgacctgcgtgtccatctg 1440
428 Y  E  C  P  H  C  A  T  I  I  A  R  K  S  D  L  R  V  H  L
    =====================ZF7=========================
    cgtaacctgcacagccagagcccggaggagatgaagtgccgatactgtcccgctggcttc 1500
448 R  N  L  H  S  Q  S  P  E  E  M  K  C  R  Y  C  P  A  G  F
    ==========                       =====================
    catgagcgctatgcccctcattcagcaccagaggacccacaagaacgagaagaagttcaag 1560
```

Fig. 3D

```
468 H   E   R   Y   A   L   I   Q   H   Q   R   T   H   K   N   E   K   K   F   K
    =====ZF8==============================
    tgcaagcagtgcgattacgcgtgcaagcaggagcgatgcttgaaggcgcacatgcgcatg 1620
488 C   K   Q   C   D   Y   A   C   K   Q   E   R   C   L   K   A   H   M   R   M
    ==========================ZF9===========================
    cacacaggagagaagcccttctcctgcctggcctgcaacaagcacttccgacagaagcag 1680
508 H   T   G   E   K   P   F   S   C   L   A   C   N   K   H   F   R   Q   K   Q
    =                         ===================ZF10====
    ctactgaccgtgcacctgaggaagtaccatgacccgaacttcgtccccaatctgcacctg 1740
528 L   L   T   V   H   L   R   K   Y   H   D   P   N   F   V   P   N   L   H   L
    ==============================
    tgcctcaagtgtgataaacgtttctcccgctggagtaacctgcagagacacagaaagaag 1800
548 C   L   K   C   D   K   R   F   S   R   W   S   N   L   Q   R   H   R   K   K
    ======================ZF11=========================
    tgtgacccggagcatgagacgttagcccccaacaaggacaggagaccagtgacaaggaca 1860
568 C   D   P   E   H   E   T   L   A   P   N   K   D   R   R   P   V   T   R   T
    =
    caggcctcggagggagaagcaggacacaaggaaggggagcctcagtgccctggggagcag 1920
588 Q   A   S   E   G   E   A   G   H   K   E   G   E   P   Q   C   P   G   E   Q
    gctctgggccaccaaggagaagcagcggggagccagagcccagaccacggccttacctgc 1980
608 A   L   G   H   Q   G   E   A   A   G   S   Q   S   P   D   H   G   L   T   C
    gagatgatctttaacatgatggataagTGATGGATAAGTGAGCAGTCGTGCCTCTCCGTG 2040
628 E   M   I   F   N   M   M   D   K
    CAGTGGCCTCTGGGGGAAGAAACCAGTTAGAAATAAGTTCCCAGACACAGCACAGTGTTC 2100
    TCAGAGTTTGAGATAGTGTGTAGAAATGTTTGAGAGAAGGGGAAAAAAACCCTGCAGCTA 2160
    TTTCCAAAGACTTGAGTCAGAGCTCGAAGTGAAGGTGCACATATCTGGGCCCTAGCAGGT 2220
    GCCCAGAATGAGTCAGGGACAGATTCTAGGTGATACTTATGTCCACGGGGCTCAGACCA 2280
    GTTAACGCCTTGGTGGTCAGAGCAGAAAATTTTTGAGTTGTTGTACCCACCCTCAA     2340
```

Fig. 4A

| | | |
|---|---|---|
| ForN1 | GAGCCTGTGGAGCGATTAAACC | (SEQ ID NO:6) |
| RevN1 | CCGCCGCCGCTCCAC | (SEQ ID NO:7) |
| ForN2 | CTTCTTTGGCGGCAGCGGCG | (SEQ ID NO:8) |
| RevN2 | CGCGCCACACCCCCGC | (SEQ ID NO:9) |
| ForN3 | CCCCAGAACCAGAC | (SEQ ID NO:10) |
| RevN3 | ACTTCAGTCTTCATCTG | (SEQ ID NO:11) |
| ForZF1 | TGTGAGCTTTGCAGTTACAC | (SEQ ID NO:12) |
| RevZF1 | ACTGTTCTGAATGCCCTG | (SEQ ID NO:13) |
| ForZF2 | CGGCGTTCAAATTTGG | (SEQ ID NO:14) |
| RevZF2 | CGAGTACCTGTGTGTGTT | (SEQ ID NO:15) |
| ForZF3 | GTGCCCAGACTGCGA | (SEQ ID NO:16) |
| RevZF3 | AATCGCACATGGAACAC | (SEQ ID NO:17) |
| ForZF4 | TTCAAGTGTTCCATGTG | (SEQ ID NO:18) |
| RevZF4 | CTGCTGGCATAACTGCAC | (SEQ ID NO:19) |
| ForZF5 | CACATACAAGCTGAAAAGG | (SEQ ID NO:20) |
| RevZF5 | GCATCTTCATGGTACCAC | (SEQ ID NO:21) |
| ForZF6 | GTCATAGCCCGAAAAGTG | (SEQ ID NO:22) |
| RevZF6 | CGCTCATGAAACACAGC | (SEQ ID NO:23) |
| ForZF7 | GTGTGACCAGTGTGATTA | (SEQ ID NO:24) |
| RevZF7 | TTCTGGCGGAAGGTCTT | (SEQ ID NO:25) |
| ForZF8 | CAAGCGCTATCACGACC | (SEQ ID NO:26) |
| RevZF8 | TCTGCATGTCTTGCCAT | (SEQ ID NO:27) |
| ForC1 | TCCTCTGACAGTGAAAATGC | (SEQ ID NO:28) |
| RevC1 | CACAGGCTGAGGCTCTGG | (SEQ ID NO:29) |
| ForC2 | CAGAATACAGGTGCAATTG | (SEQ ID NO:30) |
| RevC2 | CACCGGTCCATCATGCTG | (SEQ ID NO:31) |
| NEWTCFOR | GCCAGTGTGGAGGCAAGTAAATTGAAG | (SEQ ID NO:32) |
| NEWTCREV | CACTGGCAACACTGAAAGGGGCGCTCCCC | (SEQ ID NO:33) |

Fig. 4B

| | | |
|---|---|---|
| MB1FOR | TCGTCATATGAAAACTCACACC | (SEQ ID NO:34) |
| MB1REV | GACGAGTTCTCCACTGGTG | (SEQ ID NO:35) |
| MB2FOR | AACATACTCATGAGAAACCC | (SEQ ID NO:36) |
| MB2REV | GAGTGCGTTCTCATGTGG | (SEQ ID NO:37) |
| MB3FOR | GAGCGCCCCTTTCAGTGT | (SEQ ID NO:38) |
| MB3REV | GCACAATGGGGACAC | (SEQ ID NO:39) |
| MB4FOR | ACCCAGAGCGGGACCATGAAA | (SEQ ID NO:40) |
| MB4REV | GACAGCAGAACAGTAGCGG | (SEQ ID NO:41) |
| MB5FOR | CATAAGAATGAGAAGAGG | (SEQ ID NO:42) |
| MB5REV | AAGTTGCTTCTGTCGGAAA | (SEQ ID NO:43) |
| MBNEWFOR | TTGTGCAGTTATGCCAGCAGG | (SEQ ID NO:44) |
| MBNEWREV | GTGCTTCTGTAAAATGTGCATC | (SEQ ID NO:45) |

BROTHER OF THE REGULATOR OF IMPRINTED SITES (BORIS)

FIELD OF THE INVENTION

This invention pertains to the cancer-testis gene family member BORIS and its use in the diagnosis, prognosis and treatment of cancer.

BACKGROUND OF THE INVENTION

The American Cancer Society estimates the lifetime risk that an individual will develop cancer is 1 in 2 for men and 1 in 3 for women. The development of cancer, while still not completely understood, can be enhanced as a result of a variety of risk factors. For example, exposure to environmental factors (e.g., tobacco smoke) might trigger modifications in certain genes, thereby initiating cancer development. Alternatively, these genetic modifications may not require an exposure to environmental factors to become abnormal. Indeed, certain mutations (e.g., insertions, deletions, substitutions; etc.) or abnormally imprinted genes can be inherited from generation to generation, thereby imparting an individual with a genetic predisposition to develop cancer.

Currently, the survival rates for many cancers are on the rise. One reason for this success is improvement in the detection of cancer at a stage at which treatment can be effective. Indeed, it has been noted that one of the most effective means to survive cancer is to detect its presence as early as possible. According to the American Cancer Society, the relative survival rate for many cancers would increase by about 15% if individuals participated in regular cancer screenings. Therefore, it is becoming increasingly useful to develop novel diagnostic tools to detect the cancer either before it develops or at an as early stage of development as possible.

One popular way of detecting cancer early is to analyze the genetic makeup of an individual to detect the presence of or to measure expression levels of a marker gene(s) related to the cancer. For example, there are various diagnostic methods that analyze a certain gene or a pattern of genes to detect cancers of the breast, tongue, mouth, colon, rectum, cervix, prostate, testis, and skin. Recently, analyzing the activity of certain DNA-binding proteins, such as the CCCTC-binding factor (CTCF), has been found to be useful in diagnosing a cancer or a predisposition to a cancer (see, e.g., U.S. Pat. No. 5,972,643). CTCF and similar DNA-binding proteins can act as transcription factors which regulate gene expression, including genes involved in cell proliferation. Normally, CTCF inhibits cell proliferation; however, a partial loss of CTCF functions caused by abnormal methylation of certain CTCF target sites, or by zinc finger mutations, has been shown to be associated with cancer.

Recent efforts have brought together the fields of genomic imprinting, DNA methylation, gene regulation through transcriptional insulators, and cancer. Genomic imprinting occurs in mammals before or during gamete formation. Certain genes are uniquely imprinted in each of a male and female parent; however, only one of these genes from either the maternal or paternal chromosome is expressed in their offspring; the other of which remains silent. The inheritance of imprinted genes is epigenetic, meaning these genes are regulated the same in the offspring as in the parent from which they derived, even if the nucleotide sequence encoding the gene(s) is not identical to the parental form (e.g., has accrued one or more mutations). As a result of this phenomenon, specific genes either are expressed or remain silent, based on their imprint.

While the molecular mechanism of imprinting is largely unknown, it appears that regions of chromosomes, rather than specific genes, are imprinted. Additionally, it has been determined that DNA methylation may play a role in this process. In vertebrates, methyl groups can be added to the carbon atom at position 5 in cytosine. These methyl groups are typically added when the dinucleotide CpG or groups of CpG (i.e., CpG islands) are present along a DNA sequence. CpG islands have primarily been observed in the 5' area of expressed genes, and, in particular, the 5' area of certain housekeeping genes (see, Bird et al., *Nature* 321:209-213 (1986)). It has been hypothesized that DNA methylation plays a role in gene regulation by increasing or decreasing the affinity of regulatory DNA-binding proteins, such as CTCF (see, Watson et al., *Molecular Biology of the Gene, Volume II:* $3^{rd}$ Ed., The Benjamin/Cummings Publishing Company, Inc., Menlo, Calif. (1987)).

The process of imprinting and DNA methylation can be understood by analyzing a commonly studied imprinted gene cluster that is regulated by CTCF, which includes the closely linked imprinted genes H19 and Igf2. These genes are oppositely imprinted on each parental chromosome. Indeed, H19 is active on the maternal chromosome with Igf2 remaining silent, while on the paternal chromosome, Igf2 is active and H19 is silent. The two genes share an enhancer region located downstream of H19. Some studies have shown that the imprinting control region (ICR) of H19 is a boundary element controlled by DNA methylation. For example, it is thought that the CTCF protein binds to the unmethylated maternal ICR, which prevents the promoters located in the Igf2 gene from interacting with the enhancers downstream of the H19 gene. This results in transcriptional silencing of Igf2. If the paternal ICR is present and methylated, CTCF is prevented from binding. This allows the enhancers to contact the promoters of the paternal Igf2, allowing the gene to be transcribed.

Recent studies have indicated that abnormal imprinting could result in the activation of certain growth factors or the inactivation of tumor suppressor genes, both of which could result in the formation of cancer. Indeed, various epigenetic alterations have been associated with cancers, including global hypomethylation, hypomethylation of individual genes, and hypermethylation of CpG islands (see, Feinberg, *PNAS*, 98(2):392-394 (2001)). Thus, it would be beneficial to identify genes which, when abnormally imprinted, lead to the development of cancer.

Accordingly, a need remains for the identification of genes and gene products which can be shown to have a strong association with cancer. Such genes and gene products can lead to the development of novel therapeutic applications, as well as to early, sensitive and accurate methods for detecting a cancer or a predisposition to a cancer in a mammal. Moreover, such methods would enable clinicians to monitor the response of a mammal to a particular treatment with greater sensitivity and accuracy. The present invention provides such therapeutic applications and methods. These and other objects and advantages of the invention, as well as additional inventive features, will be apparent from the description of the invention provided herein.

BRIEF SUMMARY OF THE INVENTION

The present invention provides an isolated or purified nucleic acid molecule consisting essentially of a nucleotide sequence encoding human BORIS or a fragment thereof comprising at least 1536 contiguous nucleotides, as well as an isolated or purified nucleic acid molecule consisting essentially of a nucleotide sequence encoding a non-human BORIS or a fragment thereof comprising at least 229 contiguous nucleotides and related vectors and cells comprising such vectors.

The invention also provides an isolated or purified polypeptide molecule consisting essentially of an amino acid sequence encoding human BORIS or a fragment thereof comprising at least 307 contiguous amino acids, as well as an isolated or purified polypeptide molecule consisting essentially of an amino acid sequence encoding a non-human BORIS or a fragment thereof comprising at least 21 contiguous amino acids, and related monoclonal antibody-producing cell lines and the monoclonal antibodies so produced. The amino acid sequences encoding human or non-human BORIS or fragments thereof can optionally be glycosylated, amidated, carboxylated, phosphorylated, esterified, N-acylated or converted into an acid addition salt and/or optionally dimerized or polymerized.

Further provided is an isolated or purified nucleic acid molecule consisting essentially of a nucleotide sequence that is complementary to a nucleotide sequence encoding human BORIS or a fragment thereof comprising at least 1536 contiguous nucleotides, as well as an isolated or purified nucleic acid molecule consisting essentially of a nucleotide sequence that is complementary to a nucleotide sequence encoding a non-human BORIS or a fragment thereof comprising at least 229 contiguous nucleotides and related vectors and host cells comprising such vectors.

Still further provided by the invention is a method of diagnosing a cancer or a predisposition to a cancer in a male mammal. The method comprises detecting a nucleic acid molecule comprising a nucleotide sequence encoding BORIS or a polypeptide molecule comprising an amino acid sequence encoding BORIS in a test sample comprising somatic cells obtained from the male mammal. The detection of the nucleic acid or polypeptide molecule encoding BORIS in the test sample is indicative of the cancer or a predisposition to the cancer in the male mammal.

The invention also provides a method of predicting a predisposition to a cancer in an offspring of a male mammal. The method comprises detecting either a mutation in a nucleic acid molecule comprising a nucleotide sequence encoding BORIS, a decreased level of a polypeptide molecule comprising an amino acid sequence encoding wild-type BORIS, or a mutation in a polypeptide molecule comprising an amino acid sequence encoding BORIS in a test sample comprising germ cells obtained from the male mammal. The detection of a mutation in the nucleic acid or polypeptide molecule encoding BORIS or a decreased level of wild-type BORIS is indicative of a predisposition to the cancer in the offspring of the male mammal.

In addition to a method of diagnosing a cancer or a predisposition to a cancer in a male mammal, the invention provides a method of diagnosing a cancer or a predisposition to a cancer in a female mammal. The method comprises detecting either of a nucleic acid molecule comprising a nucleotide sequence encoding BORIS or a polypeptide molecule comprising an amino acid sequence encoding BORIS in a test sample obtained from the female mammal. The detection of the nucleic acid or polypeptide molecule encoding BORIS in the test sample is indicative of the cancer or a predisposition to the cancer in the female mammal.

The invention further provides a method of prognosticating a cancer in a mammal and a method of assessing the effectiveness of treatment of a cancer in a mammal. In such methods, BORIS is a marker for the cancer. These methods comprise measuring the level of BORIS in a test sample comprising somatic cells obtained from the mammal. The level of BORIS in the test sample is indicative of the prognosis or the effectiveness of treatment of the cancer in the mammal wherein a decrease or no change in the level of BORIS over time is indicative of a positive prognosis or an effective treatment regimen, and, alternatively, an increase in the level of BORIS over time is indicative of a negative prognosis or an ineffective treatment regimen.

Still further provided by the invention is a method of treating prophylactically or therapeutically a mammal for a cancer. In such a method, the cancer is due to the presence of a nucleic acid molecule comprising a nucleotide sequence encoding BORIS or a polypeptide molecule comprising an amino acid sequence encoding BORIS. The method comprises providing an inhibitor of BORIS to the mammal in an amount sufficient to prophylactically or therapeutically treat the mammal for the cancer. In this regard, the present invention also provides a composition comprising an inhibitor of BORIS and a carrier.

BRIEF DESCRIPTION OF THE DRAWINGS

FIG. 1A represents the nucleotide sequence corresponding to human BORIS, SEQ ID NO:1.

FIG. 1B represents the nucleotide sequence corresponding to murine BORIS, SEQ ID NO:3.

FIG. 2A represents the amino acid sequence corresponding to human BORIS, SEQ ID NO:2.

FIG. 2B represents the amino acid sequence corresponding to murine BORIS, SEQ ID NO:4.

FIG. 3A illustrates the human BORIS cDNA sequence and its conceptual translation with the 11 zinc finger regions being double-underlined and indicated as ZF 1-11.

FIG. 3B illustrates the best-fit alignment of the human CTCF and BORIS polypeptides produced by the GCG-package of programs with zero-penalty for the gap extension with conserved zing finger regions highlighted and indicated as ZF 1-11.

FIG. 3C illustrates the best-fit alignment of the human and murine BORIS polypeptides produced by the GCG-package of programs with zero-penalty for the gap extension with conserved zinc finger regions highlighted and indicated as ZF 1-11.

FIG. 3D illustrates the murine BORIS partial cDNA sequence and its conceptual translation with the 11 zinc finger regions being double-underlined and indicated as ZF-1-11.

FIG. 4A illustrates pairs of primers corresponding to conserved CTCF cDNA sequences in vertebrates used to identify human BORIS.

FIG. 4B illustrates pairs of primers corresponding to the sequence homology of human BORIS and murine CTCF used to identify murine BORIS.

DETAILED DESCRIPTION OF THE INVENTION

The invention provides an isolated or purified nucleic acid molecule consisting essentially of a nucleotide sequence encoding human BORIS or a fragment thereof comprising at least 1536 contiguous nucleotides. Preferably, the isolated or purified nucleic acid molecule (i) encodes the amino acid sequence of SEQ ID NO:2 or a fragment thereof comprising at least 307 contiguous amino acids, (ii) consists essentially of the nucleotide sequence of SEQ ID NO:1 or a fragment thereof comprising at least 1536 contiguous nucleotides, (iii) hybridizes under highly stringent conditions to an isolated of purified nucleic acid molecule consisting essentially of the nucleotide sequence that is complementary to SEQ ID NO:1 or a fragment thereof, or (iv) shares 45% or more identity with SEQ ID NO:1.

While the isolated or purified nucleic acid molecule of the invention consists essentially of a nucleotide sequence encoding human BORIS or a fragment thereof comprising at least 1536 contiguous nucleotides, larger fragments of human BORIS are also contemplated. For example, it is suitable for the isolated or purified nucleic acid molecule of the invention to consist essentially of a nucleotide sequence encoding human BORIS or a fragment thereof comprising at least 1550 contiguous nucleotides, at least 1560 contiguous nucleotides, at least 1570 contiguous nucleotides, at least 1580 contiguous nucleotides, at least 1590 contiguous nucleotides, or even at least 1600 contiguous nucleotides. Still larger fragments of human BORIS are also contemplated, such as fragments comprising at least 1700 contiguous nucleotides, at least 1800 contiguous nucleotides, at least 1900 contiguous nucleotides, or even at least 2000 contiguous nucleotides. Generally, any size fragment is contemplated as long as the fragment comprises contiguous nucleotides spanning 45% or more, 50% or more, or even 55% or more of the nucleic acid molecule consisting essentially of a nucleotide sequence encoding human BORIS.

The invention also provides an isolated or purified polypeptide molecule consisting essentially of an amino acid sequence encoding human BORIS or a fragment thereof comprising at least 307 contiguous amino acids, either one of which is optionally glycosylated, amidated, carboxylated, phosphorylated, esterified, N-acylated or converted into an acid addition salt and/or optionally dimerized or polymerized. Preferably, the isolated or purified polypeptide molecule (i) is encoded by the nucleotide sequence of SEQ ID NO:1 or a fragment thereof comprising at least 921 contiguous nucleotides, (ii) consists essentially of the amino acid sequence of SEQ ID NO:2 or a fragment thereof comprising at least 307 contiguous amino acids, or (iii) shares 47% or more identity with SEQ ID NO:2.

While the isolated or purified polypeptide molecule on the invention consists essentially of an amino acid sequence encoding human BORIS or a fragment thereof comprising at least 307 contiguous amino acids, larger fragments of human BORIS are also contemplated. For example, it is suitable for the isolated or purified polypeptide molecule of the invention to consist essentially of an amino acid sequence encoding human BORIS or a fragment thereof comprising at least 310 contiguous amino acids, at least 320 contiguous amino acids, at least 330 contiguous amino acids, at least 340 contiguous amino acids, or even at least 350 contiguous amino acids. Still larger fragments of human BORIS are also contemplated, such as fragments comprising at least 400 contiguous amino acids, at least 450 contiguous amino acids, at least 500 contiguous amino acids, or even at least 550 contiguous amino acids. Generally, any size fragment is contemplated as long as the fragment comprises contiguous amino acids spanning 47% or more, 50% or more, or even 55% or more of the polypeptide molecule consisting essentially of an amino acid sequence encoding human BORIS.

Also provided by the invention is a nucleic acid molecule consisting essentially of a nucleotide sequence that is complementary to a nucleotide sequence encoding human BORIS or a fragment thereof comprising at least 1536 contiguous nucleotides. Preferably, such an isolated or purified nucleic acid molecule (i) is complementary to a nucleotide sequence encoding the amino acid sequence of SEQ ID NO:2, (ii) is complementary to the nucleotide sequence of SEQ ID NO:1 or a fragment thereof comprising at least 1536 contiguous nucleotides, (iii) hybridizes under highly stringent conditions to an isolated or purified nucleic acid molecule consisting essentially of SEQ ID NO:1 or a fragment thereof, or (iv) shares 45% or more identity with the nucleotide sequence that is complementary to SEQ ID NO:1.

Other forms of BORIS are also contemplated in the invention. In that respect, the invention provides an isolated or purified nucleic acid molecule consisting essentially of a nucleotide sequence encoding a non-human BORIS or a fragment thereof comprising at least 229 contiguous nucleotides. Preferably, the isolated or purified nucleic acid molecule (i) encodes the amino acid sequence of SEQ ID NO:4 or a fragment thereof comprising at least 21 contiguous amino acids, (ii) consists essentially of the nucleotide sequence of SEQ ID NO:3 or a fragment thereof comprising at least 229 contiguous nucleotides, (iii) hybridizes under moderately stringent conditions to an isolated or purified nucleic acid molecule consisting essentially of the nucleotide sequence that is complementary to SEQ ID NO:3 or a fragment thereof, or (iv) shares 23% or more identity with SEQ ID NO:1.

While the isolated or purified nucleic acid molecule of the invention consists essentially of a nucleotide sequence encoding a non-human BORIS or a fragment thereof comprising at least 229 contiguous nucleotides, larger fragments of human BORIS are also contemplated. For example, it is suitable for the isolated or purified nucleic acid molecule of the invention to consist essentially of a nucleotide sequence encoding a non-human BORIS or a fragment thereof comprising at least 235 contiguous nucleotides, at least 250 contiguous nucleotides, at least 260 contiguous nucleotides, at least 270 contiguous nucleotides, at least 280 contiguous nucleotides, or even at least 290 contiguous nucleotides. Still larger fragments of a non-human BORIS are also contemplated, such as fragments comprising at least 300 contiguous nucleotides, at least 400 contiguous nucleotides, at least 500 contiguous nucleotides, or even at least 600 contiguous nucleotides. Generally, any size fragment is contemplated as long as the fragment comprises contiguous nucleotides spanning 10% or more, 20% or more, or even 30% or more of the nucleic acid molecule consisting essentially of a nucleotide sequence encoding a non-human BORIS.

The invention also provides an isolated or purified polypeptide molecule consisting essentially of an amino acid sequence encoding a non-human BORIS or a fragment thereof comprising at least 21 contiguous amino acids, either one of which is optionally glycosylated, amidated, carboxylated, phosphorylated, esterified, N-acylated or converted into an acid addition salt and/or optionally dimerized or polymerized. Preferably, the isolated or purified polypeptide molecule (i) is encoded by the nucleotide sequence of SEQ ID NO:3 or a fragment thereof comprising at least 63 contiguous nucleotides, (ii) consists essentially of the amino acid sequence of SEQ ID NO:4 or a fragment thereof comprising at least 21 contiguous amino acids, or (iii) shares 40% or more identity with SEQ ID NO:4.

While the isolated or purified polypeptide molecule on the invention consists essentially of an amino acid sequence encoding a non-human BORIS or a fragment thereof comprising at least 21 contiguous amino acids, larger fragments of a non-human BORIS are also contemplated. For example, it is suitable for the isolated or purified polypeptide molecule of the invention to consist essentially of an amino acid sequence encoding a non-human BORIS or a fragment thereof comprising at least 25 contiguous amino acids, at least 30 contiguous amino acids, at least 35 contiguous amino acids, at least 40 contiguous amino acids, or even at least 45 contiguous amino acids. Still larger fragments of a non-human BORIS are also contemplated, such as fragments comprising at least 50 contiguous amino acids, at least 55 contiguous amino acids, at least 60 contiguous amino acids, or even at least 65 contiguous amino acids. Generally, any size fragment is contemplated as long as the fragment comprises contiguous amino acids spanning 5% or more, 10% or more, or even 15% or more of the polypeptide molecule consisting essentially of an amino acid sequence encoding a non-human BORIS.

Also provided by the invention is a nucleic acid molecule consisting essentially of a nucleotide sequence that is complementary to a nucleotide sequence encoding a non-human BORIS or a fragment thereof comprising at least 229 contiguous nucleotides. Preferably, such an isolated or purified nucleic acid molecule (i) is complementary to a nucleotide sequence encoding the amino acid sequence of SEQ ID NO:4, (ii) is complementary to the nucleotide sequence of SEQ ID NO:3 or a fragment thereof comprising at least 229 contiguous nucleotides, (iii) hybridizes under moderately stringent conditions to an isolated or purified nucleic acid molecule consisting essentially of SEQ ID NO:3 or a fragment thereof, or (iv) shares 23% or more identity with the nucleotide sequence that is complementary to SEQ ID NO:3.

It will be understood that a non-human BORIS can represent any organism other than human. Typically, the organism is a mammal, such as a rat or mouse.

By “isolated” is meant the removal of a nucleic acid or polypeptide molecule from its natural environment. By “purified” is meant that a given nucleic acid or polypeptide molecule, whether one that has been removed from nature or synthesized and/or amplified under laboratory conditions, has been increased in purity, wherein “purity” is a relative term, not “absolute purity.” A “nucleic acid molecule” is intended to encompass a polymer of DNA or RNA, (i.e., a polynucleotide), which can be single-stranded or double-stranded and which can contain non-natural or altered nucleotides. Similarly, a “polypeptide molecule” is intended to encompass a linear sequence of amino acids (i.e., a primary protein structure) but also can include secondary, tertiary, and quaternary protein structures, all of which can contain non-natural or altered amino acids.

With respect to the above isolated or purified nucleic acid molecules, it is preferred that no insertions, deletions, inversions and/or substitutions are present in the nucleic acid molecule. Such a nucleic acid molecule will code for a “wild-type” BORIS. However, it is suitable for the above isolated or purified nucleic acid molecules to comprise one or more insertions, deletions, inversions and/or substitutions. Such a nucleic acid molecule will code for a “variant BORIS”. In this respect, the invention provides an isolated or purified nucleic acid molecule consisting essentially of a nucleotide sequence encoding a variant human BORIS or a fragment thereof comprising at least 1536 contiguous nucleotides. The invention also provides an isolated or purified nucleic acid molecule consisting essentially of a nucleotide sequence encoding a variant non-human BORIS or a fragment thereof comprising at least 229 contiguous nucleotides.

Similarly, with respect to the above isolated or purified polypeptide molecules, it is preferred that no insertions, deletions, substitutions and/or abnormal post-translational modifications are present in the polypeptide molecule. Such a polypeptide molecule will code for a wild-type BORIS. However, it is suitable for the above isolated or purified polypeptide molecules to comprise one or more insertions, deletions, substitutions and/or abnormal post-translational modifications. Such a polypeptide molecule will code for a variant BORIS. In this respect, the invention provides an isolated or purified polypeptide molecule consisting essentially of an amino acid sequence encoding a variant human BORIS or a fragment thereof comprising at least 307 contiguous amino acids. The invention also provides an isolated or purified polypeptide molecule consisting essentially of an amino acid sequence encoding a variant non-human BORIS or a fragment thereof comprising at least 21 contiguous amino acids.

Preferably, the variant BORIS (human or non-human) will not differ functionally from the corresponding wild-type BORIS. For example, any insertions, deletions, inversions and/or substitutions contained within the nucleic acid molecule comprising a nucleotide sequence encoding the variant BORIS will not (i) result in the introduction of a frame-shift mutation, (2) interfere with the ability of the promoter region to direct the transcription of the nucleotide sequence, or (3) interfere with the ability of the corresponding RNA transcript to be translated into a protein. It is also preferred that the one or more substitution(s) do(es) not result in a change in an amino acid of BORIS. Alternatively, and also preferred, is that the one or more substitution(s) result(s) in the substitution of an amino acid with another amino acid of approximately equivalent size, shape and charge.

If desired, the polypeptide molecules of the invention (including variant polypeptide molecules) can be modified, for instance, by glycosylation, amidation, carboxylation, or phosphorylation, or by the creation of acid addition salts, amides, esters, in particular C-terminal esters, and N-acyl derivatives of the polypeptide molecules of the invention. The polypeptide molecules also can be dimerized or polymerized. Moreover, the polypeptide molecules can be modified to create polypeptide derivatives by forming covalent or non-covalent complexes with other moieties in accordance with methods known in the art. Covalently-bound complexes can be prepared by linking the chemical moieties to functional groups on the side chains of amino acids comprising the polypeptides, or at the N- or C-terminus.

Also with respect to the above, “will not differ functionally from” is intended to mean that the variant BORIS will have activity characteristic of the wild-type BORIS. However, the variant BORIS can be more or less active than the wild-type BORIS as desired in accordance with the present invention.

The phrase “hybridizes to” refers to the selective binding of a single-stranded nucleic acid probe to a single-stranded target DNA or RNA sequence of complementary sequence when the target sequence is present in a preparation of heterogeneous DNA and/or RNA. “Stringent conditions” are sequence-dependent and will be different in different circumstances. Generally, stringent conditions are selected to be about 20° C. lower than the thermal melting point (Tm) for the specific sequence at a defined ionic strength and pH.

The Tm is the temperature (under defined ionic strength and pH) at which 50% of the target sequence hybridizes to a perfectly matched probe.

For example, under stringent conditions, as that term is understood by one skilled in the art, hybridization is preferably carried out using a standard hybridization buffer at a temperature ranging from about 50° C. to about 75° C., even more preferably from about 60° C. to about 70° C., and optimally from about 65° C. to about 68° C. Alternately, formamide can be included in the hybridization reaction, and the temperature of hybridization can be reduced to preferably from about 35° C. to about 45° C., even more preferably from about 40° C. to about 45° C., and optimally to about 42° C. Desirably, formamide is included in the hybridization reaction at a concentration of from about 30% to about 50%, preferably from about 35% to about 45%, and optimally at about 40%. Moreover, optionally, the hybridized sequences are washed (if necessary to reduce non-specific binding) under relatively highly stringent conditions, as that term is understood by those skilled in the art. For instance, desirably, the hybridized sequences are washed one or more times using a solution comprising salt and detergent, preferably at a temperature of from about 50° C. to about 75° C., even more preferably at from about 60° C. to about 70° C., and optimally from about 65° C. to about 68° C. Preferably, a salt (e.g., such as sodium chloride) is included in the wash solution at a concentration of from about 0.01 M to about 1.0 M. Optimally, a detergent (e.g., such as sodium dodecyl sulfate) is also included at a concentration of from about 0.01% to about 1.0%.

In view of the above, "highly stringent conditions" preferably allow for from about 25% to about 5% mismatch, more preferably from about 15% to about 5% mismatch, and most preferably from about 10% to about 5% mismatch. "Moderately stringent conditions" preferably allow for from about 40% to about 15% mismatch, more preferably from about 30% to about 15% mismatch, and most preferably from about 20% to about 15% mismatch. "Low stringent conditions" preferably allow for from about 60% to about 35% mismatch, more preferably from about 50% to about 35% mismatch, and most preferably from about 40% to about 35% mismatch. With respect to the preceding ranges of mismatch, 1% mismatch corresponds to one degree decrease in the melting temperature. It is generally appreciated that the stringent conditions can be manipulated by adjusting the concentration of formamide in the hybridization reaction. For example, conditions can be rendered more stringent by the addition of increasing amounts of formamide.

The above isolated or purified nucleic acid and polypeptide molecules also can be characterized in terms of "percentage of sequence identity." In this regard, a given nucleic acid or polypeptide molecule as described above can be compared to a nucleic acid or polypeptide molecule encoding BORIS by optimally aligning the nucleotide or amino acid sequences over a comparison window, wherein the portion of the nucleotide or amino acid sequence in the comparison window may comprise additions or deletions (i.e., gaps) as compared to the reference sequence, which does not comprise additions or deletions, for optimal alignment of the two sequences. The percentage of sequence identity is calculated by determining the number of positions at which the identical nucleotide or amino acid occurs in both sequences, i.e., the number of matched positions, dividing the number of matched positions by the total number of positions in the window of comparison, and multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis.; BlastN and BlastP available from the National Center for Biotechnology Information, Bethesda, Md.; or ClustalW available from the European Bioinformatics Institute, Cambridgeshire, UK), or by inspection. Generally, in regards to human BORIS, the isolated or purified nucleic acid molecule consists essentially of a nucleotide sequence encoding human BORIS which shares 45% or more identity with SEQ ID NO:1, and the isolated or purified polypeptide molecule consists essentially of an amino acid sequence encoding human BORIS which shares 47% or more identity with SEQ ID NO:2. Similarly, in regards to a non-human BORIS, the isolated or purified nucleic acid molecule consists essentially of an nucleotide sequence encoding a non-human BORIS which shares 47% or more identify with SEQ ID NO:3, and the isolated or purified polypeptide molecule consists essentially of an amino acid sequence encoding a non-human BORIS which shares 40% or more identify with SEQ ID NO:4. It will be understood, however, that the percentage of sequence identity may vary slightly when using the different computerized programs since these programs implement different algorithms. The invention is intended to cover such variations but will generally share the percentage of sequence identities above using at least one computerized program and its respective algorithm.

The present invention also provides a vector comprising an above-described isolated or purified nucleic acid molecule. A nucleic acid molecule as described above can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987)).

Suitable vectors include those designed for propagation and expansion or for expression or both. Examples of suitable vectors include plasmids, phagemids, cosmids, viruses, and other vehicles derived from viral or bacterial sources. Preferably, the vector is a viral vector and is selected from the group consisting of an adenovirus, adeno-associated virus, retroviruses, SV40-type viruses, polyoma viruses, Epstein Barr viruses, papillomaviruses, herpes virus, vaccinia virus and polio virus. Most preferably, the vector is an adenoviral vector.

When an adenoviral vector is used in the context of the present invention, the adenoviral vector can be derived from any serotype of adenovirus. Adenoviral stocks that can be employed as a source of adenovirus can be amplified from the adenoviral serotypes 1 through 51, which are currently available from the American Type Culture Collection (ATCC, Manassas, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22-30, 32, 33, 36-39, and 42-47), subgroup E (serotype 4), subgroup F (serotypes 40 and 41), or any other adenoviral serotype. Preferably, however, an adenovirus is of serotype 2, 5 or 9. However, non-group C adenoviruses can be used to prepare adenoviral vectors for delivery of one or more non-native nucleic acid sequences to a desired tissue. Preferred adenoviruses used in the construction of non-group C adenoviral vectors include Ad12 (group A), Ad7 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030; 5,837,511; and 5,849,561 and International Patent Applications WO 97/12986 and WO 98/53087.

In preferred embodiments, the adenoviral vector of the present invention is deficient in one or more replication-essential gene functions. Regions contained within the adenoviral genome which are essential for replication include E1a, E1b, E2, E4, and L1-L5. By "deficient" is meant a disruption contained within at least one of the above-mentioned regions such that the gene product encoded by the region is produced in a reduced amount as compared to normal levels. Suitable disruptions include point mutations, substitutions, deletions, insertions, and inversions. Typically, the adenoviral vector is deficient in one or more replication-essential gene functions of the E1a, E1b, E3 and/or E4 region.

A nucleic acid sequence encoding a marker protein, such as green fluorescent protein or luciferase also can be present in the vector. Such marker proteins are useful in vector construction and determining vector migration. Marker proteins also can be used to determine points of injection in order to efficiently space injections of a vector composition to provide a widespread area of treatment, if desired. Alternatively, a nucleic acid sequence encoding a selection factor, which also is useful in vector construction protocols, can be part of the adenoviral vector.

Negative selection genes may be incorporated into any of the above-described vectors. A preferred embodiment is an HSV tk gene cassette (Zjilstra et al., *Nature*, 342: 435 (1989); Mansour et al., *Nature*, 336: 348 (1988); Johnson et al., *Science*, 245: 1234 (1989); Adair et al., *PNAS*, 86: 4574 (1989); Capecchi, M., *Science*, 244: 1288 (1989), incorporated herein by reference) operably linked to a viral promoter in a viral vector. The tk expression cassette (or other negative selection expression cassette) is inserted into the viral genome, for example, as a replacement for a substantial deletion of a non-essential viral gene. Other negative selection genes will be apparent to those of skill in the art.

The vector of the present invention can comprise a native or non-native regulatory sequence operably linked to an isolated or purified nucleic acid molecule as described above. If more than one nucleotide sequence is included in the nucleic acid molecule, each sequence can be operably linked to its own regulatory sequence. The "regulatory sequence" is typically a promoter sequence or promoter-enhancer combination, which facilitates the efficient transcription and translation of the nucleic acid to which it is operably linked. The regulatory sequence can, for example, be a mammalian or viral promoter, such as a constitutive or inducible promoter. Exemplary viral promoters which function constitutively in eukaryotic cells include, for example, promoters from the simian virus, papilloma virus, adenovirus, human immunodeficiency virus, Rous sarcoma virus, cytomegalovirus, Moloney leukemia virus and other retroviruses, and Herpes simplex virus. Other constitutive promoters are known to those of ordinary skill in the art. The promoters useful as regulatory sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art and can be used in the context of the invention, when desired. The selection of promoters, e.g., strong, weak, inducible, tissue-specific and developmental-specific, is within the skill in the art. Similarly, the combining of a nucleic acid molecule as described above with a promoter is also within the skill in the art.

The term "operably linked" as used herein can be defined when a nucleic acid molecule and the regulatory sequence are covalently linked in such a way as to place the expression of the nucleotide coding sequence under the influence or control of the regulatory sequence. Thus, a regulatory sequence would be operably linked to a nucleic acid molecule if the regulatory sequence were capable of effecting transcription of that nucleic acid molecule such that the resulting transcript is translated into the desired protein or polypeptide.

The present invention further provides a cell (i.e., a host cell) comprising an isolated or purified nucleic acid molecule or a vector as described above. Examples of host cells include, but are not limited to, a prokaryotic or eurkaryotic host cell. Prokaryotic cells include those derived from *E. coli*, *B. subtilis*, *P. aerugenosa*, *S. cerevisiae*, and *N. crassa*. Preferably, the host cell is derived from a mammal, such as a human.

Cell lines producing monoclonal antibodies also are contemplated in the invention. Such "hybridoma cell lines" desirably produce a monoclonal antibody that is specific for BORIS. Methods of making hybridomas are known in the art (see, e.g., Roitt I., *Immunology*, $4^{th}$ Ed., Mosby, N.Y. (1996)). Thus, the present invention also provides a monoclonal antibody produced by the hybridoma cell line. Typically, the monoclonal antibody will be specific for a region of BORIS or a region of a variant BORIS, wherein the region comprises any region other than one encoding a conserved zinc finger region (e.g., other than one spanning amino acids 259-568) of the particular targeted BORIS. Typically, the region will be the N- or C-terminal portion of BORIS, which are unique (i.e., not conserved) regions in their respective organisms. Alternatively, the antibody can be specific for a zinc finger region of BORIS. Such an antibody will have a greater affinity for zinc finger regions of BORIS as compared to other proteins containing similar zinc finger regions (e.g., CTCF); thus being able to distinguish between the two molecules. Monoclonal antibodies of the invention can be employed for both diagnostic and therapeutic applications as they are described herein.

BORIS is a DNA-binding protein that has been mapped to the cancer-associated region 20q13 within the human genome. It has been shown to contain the same exons encoding the 11 zinc finger domain as mammalian CTCF genes while being completely divergent at the amino and carboxy termini. This indicates that the nucleoprotein complexes generated by BORIS and CTCF bind to the same target DNA sites but are likely to have distinct functions. BORIS and CTCF are expressed in a mutually exclusive pattern that correlates with re-setting of methylation marks during male germ cell differentiation, thus suggesting that BORIS directs epigenetic reprogramming at CTCF target sites. Male germ cells in which reprogramming of imprinting occurs is positive for BORIS but negative for CTCF, which provides the opportunity for BORIS to set paternally imprinted insulator sites that are later read by CTCF. The expression of BORIS in spermatocytes could reflect a demethylation of its promoter. Alternatively, BORIS could be associated with demethylases that participate in the erasure of methylation marks. It is also possible that BORIS activation is intimately linked with initiating de novo methylation. In that respect, it is possible that BORIS interacts with the Suv39h2 histone H3 methyltransferase, which marks chromatin for de novo methylation and is co-expressed with BORIS. In any event, at later stages of spermatogenesis, BORIS is silenced while CTCF is re-activated.

It has been determined that BORIS belongs to the "cancer-testis" (CT) gene family because it is aberrantly activated in substantial proportions of different cancers. The CT gene family combines genes that are normally expressed only in testis but frequently activated in different malignancies. Most, but not all, of CT-family genes encode human tumor antigens recognized by T cells. These genes include the MAGE, GAGE, and LAGE/ESO-1 CT-subgroups. A few recently discovered CT antigens are nuclear factors. However, BORIS is a unique member of the CT gene family because, in contrast to all other CT-genes, it has a somatic counterpart, CTCF, that has anti-proliferative properties and shares with BORIS homologous ZFs capable of mediating binding to overlapping sets of DNA targets. Abnormal function of BORIS due to mutations in the nucleotide sequence encoding it, such as the DNA-recognition domain, could result in an abnormal pattern of gene imprinting, a phenomenon that is known to be frequently associated with different cancers. Moreover, since BORIS has been shown to share the same unique DNA-binding sequences as CTCF, abnormal activation of BORIS in somatic cells may compete with the normal function of CTCF, leading to uncontrolled cell proliferation.

In view of the above, the invention provides a method of diagnosing a cancer or a predisposition to a cancer in a male mammal. One such method comprises detecting either (i) a nucleic acid molecule comprising a nucleotide sequence encoding BORIS or (ii) a polypeptide molecule comprising an amino acid sequence encoding BORIS in a test sample comprising somatic cells obtained from the male mammal. The detection of (i) or (ii) in the test sample is indicative of the cancer of a predisposition to the cancer in the mammal.

As indicated above, abnormal imprinting has been shown to have a relationship with the development of cancer. Accordingly, the invention provides a method of predicting a predisposition to a cancer in an offspring of a male mammal comprising detecting either (i) a mutation in a nucleic acid molecule comprising a nucleotide sequence encoding BORIS, (ii) a decreased level of a polypeptide molecule comprising an amino acid sequence encoding wild-type BORIS, or (iii) a mutation in a polypeptide molecule comprising an amino acid sequence encoding BORIS in a test sample comprising germ cells obtained from the male mammal. The detection of (i), (ii), or (iii) in the test sample is indicative of the cancer or a predisposition to the cancer in the offspring of the male mammal.

BORIS is generally expressed only in the germ cells of males. Thus, the activation of BORIS in any cell type contained in a female mammal is abnormal. Accordingly, a female mammal also can be diagnosed with a cancer or a predisposition to a cancer utilizing a method of the invention. Such a method comprises detecting either (i) a nucleic acid molecule comprising a nucleotide sequence encoding BORIS or (ii) a polypeptide molecule comprising an amino acid sequence encoding BORIS in a test sample obtained from the female mammal. The detection of (i) or (ii) in the test sample is indicative of the cancer or a predisposition to the cancer in the female mammal.

The test sample used in conjunction with the invention can be any of those typically used in the art and will vary depending on the condition of the mammal (i.e., whether or not a cancer has developed in the mammal). For example, the test sample can be tissue, which tissue comprises somatic cells. If the test sample is obtained from a male mammal, the test sample can be sperm cells or cells giving rise to sperm. Typically, the tissue is metastatic (e.g., cancerous) and is obtained by means of a biopsy. Such tissue can include bone marrow, lymph nodes, skin, and any organ that may develop cancerous cells. If the test sample is obtained from a male mammal, the test sample can be taken from the testes of the male mammal. Preferably, however, the test sample is one which is least invasive to the mammal, such as a blood sample.

A number of assays are contemplated for use in analyzing a given test sample of the present invention. As used herein, the term "assay" can be defined as any quantitative or qualitative analysis of a nucleic acid or polypeptide molecule that is known in the art. A variety of these assays are contemplated for use in the invention, many of which are described in Sambrook et al., *Molecular Cloning: A Laboratory Manual*, $2^{nd}$ Ed., Cold Spring Harbor Press, Cold Spring Harbor, N.Y., (1989). Microarrays, such as those described in U.S. Pat. Nos. 6,197,506 and 6,040,138, also can be used to detect and quantify BORIS. It will be understood that the type of assay used will depend on whether a nucleic acid or polypeptide molecule is being assayed for and whether the detection or quantification of the nucleic acid or polypeptide molecule is sought.

When a nucleic acid molecule encoding a nucleotide sequence encoding BORIS is assayed for, various assays can be used to detect or to measure the level of BORIS in a given test sample. For example, when only the detection of BORIS or the identification of a mutation in BORIS is necessary to diagnose effectively the cancer or a predisposition to the cancer, assays including PCR and microarray analysis can be used. In certain embodiments it may be necessary to detect the quantity of BORIS present. In such instances, it will be advantageous to use various hybridization techniques known in the art that can effectively measure the level of BORIS in a test sample. When BORIS comprises DNA, such hybridization techniques can include, for example, Southern hybridization (i.e., a Southern blot), in situ hybridization and microarray analysis. Similarly, when BORIS comprises RNA, Northern hybridization (i.e., a Northern blot), in situ hybridization and microarray analysis are contemplated.

It will be understood that, in such assays, a nucleotide sequence that specifically binds to or associates with a nucleic acid molecule comprising a nucleotide sequence encoding BORIS, whether DNA or RNA, can be attached to a label for determining hybridization. A wide variety of appropriate labels are known in the art, including fluorescent, radioactive, and enzymatic labels as well as ligands, such as avidin/biotin, which are capable of being detected. Preferably, a fluorescent label or an enzyme tag, such as urease, alkaline phosphatase or peroxidase, is used instead of a radioactive or other environmentally undesirable label. In the case of enzyme tags, calorimetric indicator substrates are known which can be employed to provide a detection means visible to the human eye or spectrophotometrically to identify specific hybridization with complementary BORIS nucleic acid-containing samples.

When a nucleic acid molecule comprising a nucleotide sequence encoding BORIS is amplified in the context of a diagnostic application, the nucleic acid used as a template for amplification is isolated from cells contained in the test sample, according to standard methodologies (see, e.g., Sambrook et al., (1989), supra). The nucleic acid can be genomic DNA or fractionated or whole cell RNA. Where RNA is used, it can be desirable to convert the RNA to cDNA.

In a typical amplification procedure, pairs of primers that selectively hybridize to nucleic acids corresponding to BORIS are contacted with the nucleic acid under conditions that permit selective hybridization. Once hybridized, the nucleic acid-primer complex is contacted with one or more enzymes that facilitate template-dependent nucleic acid synthesis. Multiple rounds of amplification, also referred to as "cycles," are conducted until a sufficient amount of amplification product is produced.

Various template-dependent processes are available to amplify BORIS present in a given test sample. As with the various assays, a number of these processes are described in Sambrook et al. (1989), supra. One of the best-known amplification methods is the polymerase chain reaction (PCR). Similarly, a reverse transcriptase PCR (RT-PCR) can be used when it is desired to convert mRNA into cDNA. Alternative methods for reverse transcription utilize thermostable DNA polymerases and are described in WO 90/07641, for example.

Other methods for amplification include the ligase chain reaction (LCR), which is disclosed in U.S. Pat. No. 4,883,750; isothermal amplification, in which restriction endonucleases and ligases are used to achieve the amplification of target molecules that contain nucleotide 5'-[alpha-thio]-triphosphates in one strand (Walker et al., *Proc. Natl. Acad. Sci. USA* 89: 392-396 (1992)); strand displacement amplification (SDA), which involves multiple rounds of strand displacement and synthesis, i.e., nick translation; and repair chain reaction (RCR), which involves annealing several probes throughout a region targeted for amplification, followed by a repair reaction in which only two of the four bases are present. The other two bases can be added as biotinylated derivatives for easy detection. Target-specific sequences also can be detected using a cyclic probe reaction (CPR). In CPR, a probe having 3' and 5' sequences of non-specific DNA and a middle sequence of specific RNA is hybridized to DNA, which is present in a sample. Upon hybridization, the reaction is treated with RNase H, and the products of the probe are identified as distinctive products, which are released after digestion. The original template is annealed to another cycling probe and the reaction is repeated. A number of other amplification processes are contemplated; however, the invention is not limited as to which method is used.

Following amplification of BORIS, it can be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al. (1989), supra.

Alternatively, chromatographic techniques can be employed to effect separation. There are many kinds of chromatography which can be used in the context of the present inventive methods e.g., adsorption, partition, ion-exchange and molecular sieve, and many specialized techniques for using them including column, paper, thin-layer and gas chromatography (Freifelder, *Physical Biochemistry Applications to Biochemistry and Molecular Biology*, $2^{nd}$ Ed., Wm. Freeman and Co., New York, N.Y. (1982)).

Amplification products must be visualized in order to confirm amplification of the BORIS sequence. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified BORIS sequence. The probe preferably is conjugated to a chromophore but may be radiolabeled. In another embodiment, the probe is conjugated to a binding partner, such as an antibody or biotin, where the other member of the binding pair carries a detectable moiety (i.e., a label).

One example of the foregoing is described in U.S. Pat. No. 5,279,721, which discloses an apparatus and method for the automated electrophoresis and transfer of nucleic acids. The apparatus permits electrophoresis and blotting without external manipulation of the gel and is ideally suited to carrying out methods according to the present invention.

It will be understood that the probes described above are limited in as much as any nucleic acid molecule comprising a nucleotide sequence can be used as long as the nucleic acid molecule comprising the nucleotide sequence is hybridizable to nucleic acid molecules comprising a nucleotide sequence encoding BORIS or a fragment thereof. For example, a nucleic acid of partial sequence can be used to quantify the expression of a structurally related gene or the full-length genomic or cDNA clone from which it is derived.

When a polypeptide molecule comprising an amino acid sequence encoding BORIS is assayed, various assays (i.e., immunobinding assays) are contemplated to either detect or to measure the level of BORIS in a given test sample. In such embodiments, BORIS, or an antibody able to recognize antibodies that are specific for BORIS (i.e., an anti-idiotypic antibody), can be employed to detect antibodies having reactivity therewith, or, alternatively, antibodies can be prepared and employed to detect BORIS or an anti-idiotypic antibody thereof. The steps of various useful immunodetection assays have been described in Nakamura et al., *Handbook of Experimental Immunology* ($4^{th}$ Ed.), Wol. 1, Chapter 27, Blackwell Scientific Publ., Oxford (1987); Nakamura et al., *Enzyme Immunoassays: Heterogenous and Homogenous Systems*, Chapter 27 (1987) and include Western hybridization (i.e., Western blots), immunoaffinity purification, immunoaffinity detection, enzyme-linked immunosorbent assay (e.g., an ELISA), and radioimmunoassay. A microarray also can be used to detect or measure the levels of BORIS.

In general, the immunobinding assays involve obtaining a test sample suspected of containing a polypeptide molecule comprising an amino acid sequence encoding BORIS, and contacting the test sample with an antibody in accordance with the present invention, as the case may be, under conditions effective to allow the formation of immunocomplexes. Indeed, a mammal can be diagnosed with a cancer or a predisposition to a cancer by either detecting or quantifying the levels of a polypeptide molecule comprising an amino acid sequence encoding BORIS, or an antibody that recognizes an antibody that is specific for BORIS.

Any suitable antibody can be used in conjunction with the present invention. Typically, the antibody is specific for BORIS, however, the antibody can recognize other antibodies (i.e., an anti-idiotypic antibody) present in a test sample that bind to BORIS. The antibody can be a polyclonal or a monoclonal antibody and can be identified using methods well known in the art.

The immunobinding assays for use in the present invention include methods for detecting or quantifying the amount of BORIS in a test sample, which methods require the detection or quantitation of any immune complexes formed during the binding process. Here, a test sample suspected of containing a polypeptide molecule comprising an amino acid sequence encoding BORIS would be obtained from a mammal and subsequently contacted with an antibody. The detection or the quantification of the amount of immune complexes formed under the specific conditions is then performed.

Contacting the test sample with an antibody that recognizes BORIS or an antibody that recognizes an antibody that is specific for BORIS under conditions effective and for a period of time sufficient to allow formation of immune complexes (primary immune complexes) is generally a matter of simply adding the antibody to the sample and incubating the mixture for a period of time long enough for the antibodies to form immune complexes with, i.e., to bind to, BORIS or an antibody that is specific for BORIS. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well-known in the art and can be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837, 3,850,752, 3,939,350, 3,996,345, 4,277,437, 4,275,149 and 4,366,241. Of course, additional advantages can be realized by using a secondary binding ligand, such as a second antibody or a biotin/avidin ligand binding arrangement, as is known in the art.

Alternatively, the first added component that becomes bound within the primary immune complexes can be detected by means of a second binding ligand that has binding affinity for the first antibody. In these cases, the second binding ligand is, itself, often an antibody, which can be termed a "secondary" antibody. The primary immune complexes are contacted with the labeled, secondary binding ligand, or antibody, under conditions effective and for a period of time sufficient to allow the formation of secondary immune complexes. The secondary immune complexes are then washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed.

It will be understood that other diagnostic tests can be used in conjunction with the diagnostic tests described herein to enhance further the accuracy of diagnosing a cancer or a predisposition to a cancer in a mammal. For example, a monoclonal antibody which is known to be specific for a cancer can be used in conjunction with the methods of the invention, or the detection of other genetic abnormalities known to be associated with cancer or a predisposition to a cancer can be employed.

In addition to diagnosing a cancer or a predisposition to a cancer, the present invention also provides a method of prognosticating a cancer in a mammal, wherein BORIS is a marker for the cancer, which method comprises measuring the level of BORIS in a test sample comprising somatic cells obtained from the mammal, wherein the level of BORIS in the test sample is indicative of the prognosis of the cancer in the mammal. The level of BORIS in the test sample can be measured by comparing the level of BORIS in another test sample obtained from the mammal over time in accordance with the methods described above. An increase in BORIS levels from one sample to the next is indicative of growth and/or metastasis of the cancer (i.e., a negative prognosis), whereas no change or a decrease in BORIS levels from one sample to the next is indicative of halted growth or even reduction of the cancer (i.e., a positive prognosis).

The invention also provides a method of assessing the effectiveness of treatment of a cancer in a mammal, wherein BORIS is a marker for the cancer, which method comprises measuring the level of BORIS in a test sample comprising somatic cells obtained from the mammal, wherein the level of BORIS in the test sample is indicative of the effectiveness of the treatment of the cancer in the mammal. The level of BORIS in the test sample can be measured by comparing the level of BORIS in the test sample to the level of BORIS in another test sample obtained from the mammal over time in accordance with the methods described above. An increase in BORIS levels from one sample to the next is indicative of the treatment being ineffective, whereas no change or a decrease in BORIS levels from one sample to the next is indicative of the treatment being effective.

As used herein, the term "decreased level" can be defined as detecting BORIS in a test sample obtained from a mammal at a level below that which is considered normal. For example, the level of BORIS in a test sample is decreased when the copy number of the gene encoding BORIS, the mRNA encoding BORIS, or a polypeptide molecule comprising an amino acid sequence encoding BORIS is detected at a level below that which is considered normal. Conversely, the term "increased level" can be defined as detecting BORIS in a test sample obtained from a mammal at a level above that which is considered normal. For example, the level of BORIS in a test sample is increased when the copy number of the gene encoding BORIS, the mRNA encoding BORIS, or a polypeptide molecule comprising an amino acid sequence encoding BORIS is detected at a level above that which is considered normal. "Normal levels" pertain to an already determined range of BORIS established from cancer-free mammals of the same species and are generally accepted and recognized in the art.

The present invention further provides a method of treating a mammal prophylactically or therapeutically for a cancer by administering to the mammal an inhibitor of BORIS. Typically, the cancer is due to the presence of (i) a nucleic acid molecule comprising a nucleotide sequence encoding BORIS or (ii) a polypeptide molecule comprising an amino acid sequence encoding BORIS. An inhibitor of (i) or (ii) can be administered to the mammal in an amount sufficient to treat prophylactically or therapeutically the mammal for the cancer. For example, if the cancer is due to the presence of (i), a corresponding inhibitor of (i) can be provided to the mammal by administering to the mammal an antisense or a ribozyme molecule specific for (i), wherein the antisense or ribozyme molecule inhibits (i) after being administered to the mammal. Alternatively, if the cancer is due to the presence of (ii), an inhibitor of (ii) can be provided to the mammal by administering to the mammal a small molecule or an antibody specific for (ii), wherein the small molecule or antibody inhibits (ii) after being administered to the mammal.

By "prophylactic" is meant the protection, in whole or in part, against a particular pathologic state. By "therapeutic" is meant the amelioration of a pathologic state, itself, and the protection, in whole or in part, against further infection. One of ordinary skill in the art will appreciate that any degree of protection from, or amelioration of, a pathologic state is beneficial to a mammal.

A male or female mammal can be diagnosed with, or predisposed to, any cancer utilizing the methods of the invention. Similarly, the methods involving prognosticating a mammal for a cancer, assessing the effectiveness of treatment of a cancer, and treating a mammal prophylactically or therapeutically for a cancer can be utilized with any cancer. Preferably, the cancer is of epithelial origin and can include: lung cancer; renal cancer; anal cancer; bile duct cancer; bladder cancer; bone cancer; brain and spinal chord cancers; breast cancer; cervical cancer; lymphoma; colon and rectal cancer; endometrial cancer; esophageal cancer; gallbladder cancer; gastrointestinal cancer; laryngeal cancer; leukemia; liver cancer; multiple myeloma; neuroblastoma; ovarian cancer; pancreatic cancer; prostatic cancer; retinoblastoma; skin cancer (e.g., melanoma and non-melanoma); stomach cancer; testicular cancer; thymus cancer; thyroid cancer; as well as other carcinomas and sarcomas.

In view of the above, the present invention also provides a composition comprising a carrier and either (i) an above-described isolated or purified nucleic acid molecule and corresponding fragments thereof, (ii) an above-described vector, (iii) an above-described polypeptide molecule and corresponding fragments thereof, or (iv) an above-described inhibitor of BORIS. The inhibitor of BORIS can be any compound and/or molecule or any other agent capable of inhibiting the normal function of BORIS. Typically, the inhibitor of BORIS is a small molecule, an antibody, an antisense molecule, or a ribozyme molecule. It is also conceivable to provide an inhibitor of BORIS, which comprises a molecule (e.g., a zinc finger binding protein) that recognizes zinc finger binding domains specific for BORIS and can therefore initiate its inhibition. It will be understood that when such zinc finger binding proteins are used, these molecules will be employed to specifically recognize zinc finger binding domains of BORIS as compared to other proteins comprising similar zinc finger binding domains (e.g., CTCF), such that the normal function of these similar proteins is not inhibited. Methods of identifying these inhibitors are well known in the art and can be accomplished without any undue experimentation using a variety of in vitro assays.

The composition can comprise more than one active ingredient, such as comprising more than one inhibitor of BORIS. Alternatively, or additionally, the composition can comprise another pharmaceutically active agent or drug. For example, when treating cancer, other anticancer compounds can be used in conjunction with the composition of the present invention and include, but are not limited to, all of the known anticancer compounds approved for marketing in the United States and those that will become approved in the future. See, for example, Table 1 and Table 2 of Boyd, Current Therapy in Oncology, Section 1. Introduction to Cancer Therapy (J. E. Niederhuber, ed.), Chapter 2, by B. C. Decker, Inc., Philadelphia, 1993, pp. 11-22. More particularly, these other anticancer compounds include doxorubicin, bleomycin, vincristine, vinblastine, VP-16, VW-26, cisplatin, carboplatin, procarbazine, and taxol for solid tumors in general; alkylating agents, such as BCNU, CCNU, methyl-CCNU and DTIC, for brain or kidney cancers; and antimetabolites, such as 5-FU and methotrexate, for colon cancer.

The carrier can be any suitable carrier. Preferably, the carrier is a pharmaceutically acceptable carrier. With respect to compositions, the carrier can be any of those conventionally used and is limited only by chemico-physical considerations, such as solubility and lack of reactivity with BORIS, and by the route of administration. It will be appreciated by one of skill in the art that, in addition to the above-described composition, the compositions of the present inventive methods can be formulated as inclusion complexes, such as cyclodextrin inclusion complexes, or liposomes.

The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the BORIS and one which has no detrimental side effects or toxicity under the conditions of use.

The choice of carrier will be determined in part by the particular BORIS or inhibitor of BORIS involved, as well as by the particular method used to administer the composition. Accordingly, there are a variety of suitable formulations of the composition of the present invention. The following formulations for oral, aerosol, parenteral, subcutaneous, intravenous, intramuscular, interperitoneal, rectal, and vaginal administration are exemplary and are in no way limiting.

One skilled in the art will appreciate that suitable methods of administering a composition of the invention to a mammal, in particular a human, are available, and, although more than one route can be used to administer a particular compound, a particular route can provide a more immediate and more effective reaction than another route. Accordingly, the herein-described methods are exemplary and are in no way limiting.

The dose administered to a mammal, in particular a human, should be sufficient to treat prophylactically or therapeutically the cancer in the mammal. One skilled in the art will recognize that dosage will depend upon a variety of factors including the strength of the particular composition employed, as well as the age, species, condition, and body weight of the mammal. The size of the dose will also be determined by the route, timing, and frequency of administration as well as the existence, nature, and extent of any adverse side-effects that might accompany the administration of a particular composition and the desired physiological effect.

Suitable doses and dosage regimens can be determined by conventional range-finding techniques known to those of ordinary skill in the art. Generally, a composition is initially administered in smaller dosages, which are less than the optimum dose of the composition. Thereafter, the dosage is increased by small increments until the optimum effect under the circumstances is reached. The present inventive method will typically involve the administration of about 0.1-100 mg of one or more of the compositions described above per kg body weight.

EXAMPLES

The following examples serve to illustrate the present invention and are not intended to limit its scope in any way.

Example 1

This example demonstrates the isolation, identification and characterization of the human and murine BORIS cDNA sequences.

Comparative electrophoretic mobility shift assays (EMSAs) of nuclear extracts (NEs) were prepared from total rat testis and liver. Several well-characterized CTCF-target sequences were utilized as EMSA probes (see, e.g., Ohlsson et al., *Trends Genet.*, 17:520-527 (2001)). Specifically, NEs from rat or mouse testis and liver tissues were prepared essentially according to the protocol of Lichtsteiner et al. (see, Lichtsteiner et al., *Cell*, 51: 963-973 (1987)), but with addition of protease and phosphatase inhibitors (see, e.g., Klenova et al., *Mol Cell Biol*, 13: 7612-7624 (1993) and Lobanenkov et al., *Oncogene*, 5: 1743-1753 (1990)). The same inhibitors were present in all other protein-containing solutions unless otherwise indicated. NEs from cultured cell lines were obtained with a NUN-buffer containing 0.3M NaCl, 1M urea, and 1% nonionic detergent Nonidet P-40 (see, e.g., Klenova et al., *J Biol Chem*, 273:26571-26579 (1998) and Filippova et al., *Mol Cell Biol*, 16:2802-2813 (1996)). The length and sequence of each DNA fragment used as a probe for EMSA, and labeling and purification of the probes, were essentially as detailed in Kanduri et al., *Curr Biol*, 10:853-856 (2000) and in Filippova et al., *Cancer Research*, 62: available online (2002). Binding reactions for EMSA were carried out in a buffer containing phosphate buffered saline (PBS) with 5 mM $MgCl_2$, 0.1 mM $ZnSO_4$, 1 mM DTT, 0.1% Nonidet P-40 and 10% glycerol in the presence of poly(dI-dC), double-stranded poly(dG)-poly(dC), and a 44-mer oligonucleotide 5'-CTAGAGCCCCTCGGCCGCCCCCTCGCGGCGCGC-CCTCCCCGCTT-3' (SEQ ID NO:5). Such an oligonucleotide harbors overlapping binding sites for Sp1, Egr1 (Zif268) and "poly-G"-binding nuclear factors which can bind to the relatively short GC-rich segments within the extended CTCF sites. Reaction mixtures of 20 µl were incubated for 30 minutes at room temperature and then analyzed on 5% nondenaturing PAGE run in 0.5× trisborate-EDTA buffer. For super-shifting EMSA experiments, antibodies in PBS were added to the protein-DNA binding reactions. Results obtained from testis NEs revealed a DNA-protein complex with electrophoretic mobility slightly slower than that for the CTCF complex. This activity was not detected in NEs prepared from rat liver cells, or from a variety of other somatic tissues from rats and mice.

The binding activity found only in testis NEs exhibited DNA-binding properties like those of CTCF. Indeed, binding activity in testis NEs could be observed only with DNA probes bearing known CTCF-target sequences, such as the FII insulator site from the chicken globin locus (Bell et al., *Cell*, 98:387-396 (1999)). This activity could be competed with an excess of unlabeled DNA fragments bearing other CTCF targets, but not with the same fragments mutagenized at specific CTCF-contacting bases (see e.g., Kanduri et al., supra, Filippova et al., *Nat Genet*, 28:335-343 (2001), Klenova et al. (1993), supra, Filippova et al. (1996), supra, and Awad et al., *J Biol Chem*, 274:27092-27098 (1999)), or with the same molar excess of additional control DNA fragments of λ-phage DNA digested with HindIII.

It was also found that, like CTCF, the testis-specific factor could be "supershifted" in EMSAs with an excess of affinity-purified antibodies against the bacterially-expressed, His-tagged, C-terminal part of human CTCF, the region beginning from the middle of the 11$^{th}$ zinc finger region (ZF) and ending at the stop codon. However, in contrast to DNA-bound CTCF, this testis-specific DNA-binding activity could not be supershifted by affinity-purified antibodies against the conserved N-terminal region of CTCF upstream of the first ZF. Taken together, these results suggest that in addition to CTCF, nuclear extracts from testis contained a different form of CTCF or a protein highly related to CTCF.

To identify the human testis-specific CTCF-like protein(s), a variety of oligonucleotides homologous to regions of sequence identity found in the frog, chicken, mouse, rat, and human CTCF cDNAs were designed by the Pile-up and Pretty plot algorithms of the Wisconsin GCG package. Specifically, frog, chicken, mouse, rat, and human CTCF cDNA sequences, as well as *Drosophila* CTCF cDNA (GenBank accession # AF313621; J. Moore, G. Filippova, and V.V.L., unpublished results) were all included in a search for exceptionally conserved short DNA segments for use in designing the PCR-screening primers listed in FIG. 4A. These were used in numerous combinations in attempts to PCR-amplify human testis-specific CTCF-like cDNA fragments. As a template, the "MARATHON®-Ready" human testis cDNA (Clontech, Palo Alto, Calif.; cat# 7415-1) was used. Annealing temperatures were adjusted according to the lowest Tm of the primer in each pair minus 6° C. Each combination of primer pairs was utilized to work with a MASTERAMP™ PCR Optimisation Kit (Epicentre Technologies, cat#M07201). PCR products were analyzed on agarose gels. Distinct DNA-bands were purified and cloned into pCR 2.1-TOPO vector (Invitrogen) and subsequently sequenced. Over a hundred of resulting fragments were cloned into the vector and sequenced. One such fragment displayed a novel human cDNA sequence containing an ORF encoding CTCF-like ZFs. This sequence served to design the new pairs of primers, NEW/TC/for and NEW/TC/rev (FIG. 5A), for a stringent PCR analyses of the "Rapid Screen Arrayed human testis cDNA Library Panel" (Origene), as well as for the 5'- and 3'-RACE with the MARATHON®-Ready testis cDNA and adaptor primers from the MARATHON® cDNA Amplification kit (Clontech, Palo Alto, Calif.). This resulted in isolation of a near-full length BORIS cDNA insert in the pCMV6 vector, and of the cDNA sequence shown in FIG. 1A. 5' RACE was performed using GENERACER™ kit (Invitrogen cat# 45-0079) according to the manufacturers instructions. A similar strategy, but based on the finding of near-identical nucleotide sequences in human BORIS and in the murine CTCF cDNAs was used to design pairs of primers, listed in FIG. 4B, for a PCR-mediated screening for the mouse homologue in the MARATHON®-ready mouse testes cDNA libraiy (Clontech, Palo Alto, Calif.). Again, after obtaining and sequencing a fragment encoding the mouse BORIS ZF region, new internal specific primers combined with those from the MARATHON® cDNA Amplification kit were utilized to subclone and sequence the 5' and 3' termini of the mouse cDNA. This resulted in the murine BORIS cDNA sequence shown in FIG. 1B that extends to the polyA end, but truncates at the 5'-UTR. Specific methods for 5'-RACE over "difficult" GC-rich region will be used to complete sequence of the 5'-UTR.

Example 2

This example further demonstrates that BORIS expression is testis-specific.

Human and mouse tissues were analyzed for expression of BORIS mRNA by hybridization of Northern blots and by RT-PCR with cDNAs prepared commercially. To probe Northern blots, the NdeI-AccI fragment of the 5' end of human CTCF cDNA clone p7.1 and XhoI-XhoI fragment of the BORIS cDNA were used. For analyses of the normal expression patterns, human BORIS-specific primers (Forward, 5'-caggccctacaagtgtaacgactgcaa-3' (SEQ ID NO:46) and Reverse, 5'-gcattcgtaaggcttctcacctgagtg-3' (SEQ ID NO:47)) were used to amplify human BORIS by PCR. Similarly, mouse BORIS-specific primers (Forward, 5'-gagagacagacaagagagaagagaggttgctc-3' (SEQ ID NO:48) and Reverse, 5'-cctgtgtgggtgttcacatggttcctaagaag-3' SEQ ID NO:49)) were used to amplify mouse BORIS by PCR. Amplification of human and mouse β-actin with primers provided by OriGene was performed in parallel as a control to normalize for gel-loading differences.

In sum, these studies demonstrate that expression of BORIS transcripts is strictly testis-specific in both mouse and human. It is worth noting that, even with the high sensitivity of the RT-PCR method, BORIS expression was below the limits of detection in mouse or human ovaries, and in tissues of 8.5-day to 19-day mouse embryos.

Example 3

This example demonstrates that BORIS maps to a position located on human chromosome 20.

For BORIS chromosome mapping, metaphase spreads were prepared from the peripheral blood leukocytes of a normal male donor according to standard procedures. The entire PAC clone RP4-579F20 (AL160176) containing most of the coding exons (or the human BORIS cDNA) was labeled with digoxygenin-11-dUTP and used as a probe for FISH using the procedure previously described in detail (see, e.g., Pack et al., Cancer Res., 59:5560-5564 (1999)). For cell typing, frozen mouse testis sections were used as a template. A mixture of the Coatosome X labeled with Spectrum Orange and Coatosome Y labeled with Spectrum Green (Vysis, Downers Grove, Ill.) was used as a probe. The DNA was denatured at 78° C. for 5 minutes and hybridized overnight in a humidified chamber at 37° C. followed by washes at 45° C. in 50% formamide/2×SSC (5-min×3), and 0.1×SSC (5 min×2), 4×SSC/0.1% Tween 20 at RT (2 min). Detection of cDNA probe was done using anti-Digoxigenin Rhodamine (Roche) or with avidin-FITC (if labeled with biotin-16-dUTP). Slides were counterstained with 0.25 mg/ml DAPI-antifade (4',6-Diamidino-2-phenylindole dihydrochloride).

As indicated above, human BORIS maps to position 20q13 on human chromosome 20, a region paralogous to CTCF-containing locus at 16q22 and orthologous to the H3-H4 region of mouse chromosome 2. Taken together with the results of genomic structure analyses, these findings provide evidence that BORIS maps to position 20q13.2 and is a CTCF paralogue.

Example 4

This example demonstrates the evolutionary origin of human BORIS, and, in particular, further demonstrates its relationship with CTCF and murine BORIS.

An optimal alignment of human BORIS and CTCF amino acid sequences (FIG. 3B) revealed a remarkable identity of the entire 11 ZFs, including all of the major DNA-base-recognition residues at positions-1, 2, 3, and 6 within each finger. ZF regions are illustrated in FIG. 3A for human BORIS and FIG. 3D for murine BORIS.

To verify that the cloned BORIS cDNA encodes the same CTCF-site-binding activity that was initially detected in testis NEs by EMSAs, the clone was used to produce a full-length recombinant BORIS in *Pichia pastoris* yeast as described earlier for CTCF (see, e.g., Quitschke et al., *Nucleic Acids Res*, 28:3370-3378 (2000)). CTCF was purified as originally described by Quitschke et. al. (2000), supra, with modifications outlined recently by Vostrov et. al., *J Biol Chem*, 8:ms M109748200 in JBC website (2001). Expression of BORIS in yeast was accomplished using the *Pichia* Expression Kit (Invitrogen Co., Carlsbad, Calif.) according to the manufacturer's instructions, with chromatography steps similar to those described for CTCF (see, e.g., Vostrov et al. (2001), supra). Briefly, BORIS cDNA EcoRI-NotI DNA fragment from the pCVM6/BORIS cDNA was re-cloned into the polycloning site of the pPIC3.5 *Pichia* vector that directs intracellular recombinant protein expression in *Pichia pastoris*. The vectors containing BORIS cDNA were transformed into *Pichia* strand KM71 by electroporation. After growth to preparative quantities (10-15 g), *Pichia* cells were homogenized with a BEAD BEATER™ apparatus (Biospec Products, Inc., Bartensville, Okla.) in buffer containing 40 mM HEPES, pH 7.6, 2 mM MgSO$_4$, 1 mM EDTA, 10 μM ZnSO$_4$, 100 mM KCl. Cell debris was pelleted at 5,000 g for 10 minutes and the supernatant was further clarified by centrifugation at 100,000 g for 30 minutes. For use as a non-specific control, wild-type *Pichia* yeast protein extract also was prepared and used as a template for coupled in vitro transcription/translation in reticulocyte lysate TnT (Promega). Positive clones were amplified, induced for protein expression and screened for the presence of BORIS by Western blotting. The resulting full-length-BORIS proteins were analyzed in EMSAs side-by-side with testis and liver NEs.

The results of the EMSAs and NEs demonstrate that recombinant BORIS forms a complex with the FII DNA generating the same-mobility EMSA-band as that produced by the endogenous BORIS from testis NEs. Conversely, recombinant full-length-CTCF produced the faster-migrating band that also is present in NEs from a variety of tissues. Similar results were obtained with the proteins produced in TnT-lysates and in *Pichia*.

The relationship between human and murine BORIS was also analyzed. The Bestfit alignment of mouse and human BORIS amino acid sequences (FIG. 3C) demonstrated that, while all 11 ZFs are practically identical, the regions outside the ZFs are only similar. The latter sequences are not as highly conserved as the regions of CTCF that flank the ZFs. While outside ZFs, CTCF proteins have >90% identical amino acids in all vertebrates from frogs to humans, these regions of mouse and human BORIS and CTCF proteins manifest no obvious homology to one another and no significant similarities to other proteins analyzed by the SMART search engine (http://smart.embl-heidelberg.de).

Thus, the remarkable similarity of "shared" ZFs and absence of significant similarities outside the ZFs suggest that, while mammalian CTCF and BORIS recognize the same spectrum of DNA sequences, the functional consequences of DNA binding by these two proteins is likely to be different.

tumors were tested for the presence of BORIS transcripts (see Table 1 below). CTCF-specific primers served as an internal control of the quality of both RNA and first-strand cDNA.

TABLE 1

| Cancer Type | Boris Positive Cell Line | Boris Negative Cell Line |
|---|---|---|
| Breast Cancer | ZR75-1, MDA453, MDA231, MCF7/ADR-RES, HS578T, CAMA-1, MDA435, DU4475 | MCF7, MDA-MB-231, MDA-MB-435, MDA-N, T47D, BT549 |
| Colon Cancer | COLO320-HSR, DLD1, COLO205, HCC-2998 | HCT116, SW48, HCT15, HT29, KM12, SW-620 |
| Bladder Cancer | 5637, T24, J82 | None Identified |
| Erythroleukemia | K562, TF-1 | None Identified |
| Glioblastoma | U87, U3T3, SF-539, SNB-19, U251, T98G, SF-268 | SF-295, SNB-75 |
| Lymphoma | BCBL1, Hut102-TH, H9, Peer-I, SU-DHL4, SU-DHL5, SU-DHL6, SU-DHL7, SU-DHL10, Raji, Delgado, SB, NCEB, Tera-1, Daudi | L-428, Dev, KM-H2, HSB, SR, MOLT4, CEM, Jurkat, RPMI-8402, SU-DHL1, KiJK, Karpas299, SR786, Wynn, JD38, Wilson EW-36, Thomas-0, RPMI-8392, Granta, CCRF-CEM |
| Non-Small-Cell-Lung Cancer | A549, EKVX, NCI-H23, NCI-H522 | NCI-H2087, NCI-H2228, NCI-H460, NCI-H4226, NCI-H322M, HOP-92, HOP-62 |
| Melanoma | G361, 624.28-MEL, 624.38-MEL, 938-MEL, 1359-MEL, 836-MEL, A375, Godowns-MEL, LOX IMVI, MALME-3M, SK-MEL-2, SK-MEL-28, SK-MEL-5, UACC-257, UACC-62 | 1123-MEL, M14 |
| Myeloma | KMM1, KMS1, KMS5, KMS18, NCI-H929 | KMS12-BM, KMS-11, KMS20, RPMI8226, HAA1 |
| Neuroblastoma | SK-N-D2, GoTo, SK-N-SH, U118, H4C, SK-N-AS, SK-N-DZ | CLB-Ma, NBL-W, SHSY5Y |
| Ovarian Cancer | IGROV1, OVCAR-3, OVCAR-4, OVCAR-8 | OVCAR-5, SK-OV-3 |
| Prostate Cancer | Vcap, DuCap, TP2 | LNCap, PC-3, LNCap clone FGC, DU145 |
| Renal Cancer | TK-10 | RCC, 786-0, A498, ACHN, CAKI-1, SN12C, UO-31, RXF-393 |
| Rabdomyosarcoma | RH30, RDG2 | RH18, RDG7 |
| Miscellaneous Cancers | NCCIT, HeLa, U-2-OS, QMHK10, RD-ES, SK-NEP-1, JEG-36, PFSK-1 | KatoIII, SW1088, HT-3, SW872, Hep3BH, U937, HL-60 |

Example 5

This example demonstrates that BORIS is a novel "cancer-testis" gene abnormally activated in multiple malignancies and maps to a region frequently amplified in a variety of cancers.

The human chromosome 20q13.2 region that encompasses the BORIS gene is commonly amplified, or exhibits moderately gains of material, in many human cancers. This has led to the suggestion that this region contains a major oncogene or a dominant immortalizing gene(s) that can overcome senescence and promote genome instability. The localization of human BORIS to this cancer-related chromosomal locus, as well as frequent loss of gene imprinting in cancer involving abnormal methylation of CTCF target sites and possibly other mechanisms, raised the possibility that aberrant activation of BORIS expression in tissues other then testis could be associated with tumor pathogenesis.

Northern blot or RT-PCR analyses in a variety of cancer cell lines representing most of the major forms of human In total, approximately two hundred cell lines were tested. BORIS transcripts were detected in more then half (106/193) of the cell lines, although the proportions of positive lines varied widely among tumor types. Significant proportions of lymphoma, 15/37 (40%); breast cancer, 8/14 (57%); melanoma cell lines, 15/17 (88%); and of Wilms tumors, 5/9 (56%) (one cell line, and 8 primary tumor samples) expressed BORIS. Moreover, preliminary results of the BORIS expression analyses in over fifty randomly selected primary breast cancer samples demonstrated that the frequency of BORIS abnormal expression in these samples is ~50-60%. Thus, the frequency of abnormal BORIS activation in primary breast cancer is similar to that observed in breast cancer cell lines.

These results indicate that the normally strict silencing of BORIS in somatic tissues is frequently abrogated in many different cancer cell lines. Thus, it is evident that BORIS is a novel cancer-testis gene abnormally activated in multiple malignancies.

Example 6

This example demonstrates that BORIS and CTCF compete for similar DNA binding regions and that such competition promotes abnormal cell growth.

EMSA analyses with DNA probes representing CTCF-binding sequences in the H19 ICR and FII insulator site were performed. The full-length and DNA-binding 11 ZF domain versions of BORIS and CTCF were mixed in various proportions. Since the isolated 11 ZF domains of CTCF and BORIS have in vitro DNA-binding properties similar to those of the full-length proteins, each protein was represented by either a full-length polypeptide or by its 11 ZF domain to facilitate identification of the corresponding bands on EMSA gels. The addition of increasing amounts of the BORIS 11 ZF protein to EMSA reactions with constant amounts of the full-length CTCF and DNA from the H19 ICR resulted in efficient competition of CTCF/DNA complexes by BORIS. In a reverse experiment with a DNA probe containing the FII insulator site, the CTCF 11 ZF domain efficiently competed for formation of the BORIS/DNA complex. These results provide evidence that the in vivo occupancy of a common target for CTCF and BORIS will be determined by the relative levels of DNA-binding forms of these proteins in the sub-nuclear compartments where CTCF, BORIS, and a target DNA co-localize.

To test if competition with CTCF by exogenous expression of BORIS would promote growth or transform NIH3T3 cells, which normally express BORIS at levels below the limits of detection by RT-PCR, the pCIIN-BORIS expression vector was engineered as described earlier for CTCF (see, e.g., Rasko et al., *Cancer Res*, 61:6002-6007 (2001)). This construct utilizes a CMV promoter for coupled expression of both BORIS and Neo coding regions connected by an internal ribosome entry site (IRES) within one bi-cistronic message. In an attempt to establish stable BORIS-expressing cell lines, cells were transfected with 0.1 µg to 10 µg of either pCIIN-BORIS plasmid or a control vector expressing Neo but no BORIS. Less then 20 hours after transfection, marked cell death was observed in cells transfected with the BORIS-containing constructs. The numbers of residual viable cells were inversely proportional to the vector inputs. In contrast, practically no cell death was evident in cells transfected with the control vector. When RT-PCR was used to analyze total RNA prepared from cells collected one day after transfection, both BORIS and Neo parts of the bi-cistronic message were detected. In additional studies, the dead cells from cultures transfected with pCIIN-BORIS were removed, and the remaining viable cells were cultured in the presence of G418 for 14 days. Surprisingly, none of the few G418-resistant colonies recovered expressed BORIS sequence detectable by RT-PCR, but all were positive for the Neo sequence. The toxic effects of constitutive BORIS expression from a heterologous promoter were likely due to accumulation of BORIS at levels sufficient to compete with most CTCF-DNA interactions in vivo in a manner similar to that observed when mixing DNA-targets with CTCF and BORIS in vitro. This would cause a complete block of CTCF functions since the observed effect of BORIS over-expression, namely cell death, is similar to the effects caused by CTCF depletion. Therefore, only partial interference with CTCF functions may be permissive for cell immortalization and/or transformation, rather then cell death. This hypothesis is supported by the recent results of mutational analyses of CTCF in tumors selected for LOH at the locus of the human CTCF (16q22). Several ZF-specific missense point-mutations that resulted in selective alterations in target site specificities of CTCF binding were found but none of these tumors contained truncating CTCF mutations that could cause complete loss of CTCF functions.

These results indicate that BORIS and CTCF, when present together, compete for the same DNA binding sites and that such competition can lead to abnormal cell growth.

All of the references cited herein, including patents, patent applications, and publications, are hereby incorporated in their entireties by reference.

While this invention has been described with an emphasis upon preferred embodiments, variations of the preferred embodiments can be used, and it is intended that the invention can be practiced otherwise than as specifically described herein. Accordingly, this invention includes all modifications encompassed within the spirit and scope of the invention as defined by the claims.

What is claimed is:

1. An isolated or purified nucleic acid molecule comprising a nucleic acid sequence that encodes SEQ ID NO: 2.

2. The isolated or purified nucleic acid molecule of claim 1, wherein the nucleic acid molecule comprises SEQ ID NO: 1.

3. A vector comprising the isolated or purified nucleic acid molecule of claim 1.

4. An isolated cell comprising the vector of claim 3.

5. A method of diagnosing a cancer in a mammal, wherein said method comprises detecting a nucleic acid molecule comprising SEQ ID NO: 1 in a test sample comprising somatic cells obtained from the mammal, wherein the detection of the nucleic acid molecule comprising SEQ ID NO: 1 in the test sample is indicative of the cancer in the mammal.

6. A vector comprising the isolated or purified nucleic acid molecule of claim 2.

7. An isolated cell comprising the vector of claim 6.

8. The method of claim 5, wherein the cancer is breast cancer.

9. The method of claim 5, wherein the cancer is endometrial cancer.

10. The method of claim 5, wherein the test sample comprises somatic cells.

11. The method of claim 5, wherein the test sample comprises blood.

12. The method of claim 5, wherein detecting a nucleic acid comprising SEQ ID NO: 1 comprises the use of Southern blot, Northern blot, in situ hybridization, or microarray analysis.

13. The method of claim 5, wherein detecting a nucleic acid comprising SEQ ID NO: 1 comprises the use of PCR or RT-PCR.

14. A method of detecting expression of a nucleic acid sequence encoding SEQ ID NO: 2 in a mammal, which method comprises:

(a) contacting a test sample from the mammal with a nucleic acid molecule that specifically binds to the isolated or purified nucleic acid molecule of claim 1, and (b) detecting hybridization of the nucleic acid molecule used in step (a) to a nucleic acid molecule of the test sample, wherein hybridization indicates expression of a nucleic acid molecule encoding SEQ ID NO: 2.

15. The method of claim 14, wherein the nucleic acid molecule used in step (a) is attached to a label.

16. The method of claim 15, wherein the label is a fluorescent label or an enzyme tag.

17. The method of claim 14, wherein detecting hybridization comprises the use of Southern blot, Northern blot, in situ hybridization, or microarray analysis.

18. The method of claim 14 wherein detecting hybridization comprises the use of PCR or RT-PCR.

19. The method of claim 14, wherein the test sample comprises somatic cells.

20. The method of claim 14, wherein the test sample comprises blood.

21. The method of claim 14, wherein the nucleic acid that specifically binds to an isolated or purified nucleic acid of claim 1 comprises a nucleic acid sequence that is complementary to SEQ ID NO: 1.

* * * * *

SEQUENCE LISTING

```
<160> NUMBER OF SEQ ID NOS: 49

<210> SEQ ID NO 1
<211> LENGTH: 3541
<212> TYPE: DNA
<213> ORGANISM: Homo sapiens

<400> SEQUENCE: 1
accctccact ctcgcgccag cccggcggcg gccggctgtg ggctgcagca cgcggtgcac      60
gaggcagagc cacaagccaa agacggagtg ggccgagcat tccggccacg ccttccgcgg     120
ccaagtcatt atggcagcca ctgagatctc tgtcctttct gagcaattca ccaagatcaa     180
agaactcgag ttgatgccgg aaaaaggcct gaaggaggag gaaaaagacg gagtgtgcag     240
agagaaagac catcggagcc ctagtgagtt ggaggccgag cgtacctctg gggccttcca     300
ggacagcgtc ctggaggaag aagtggagct ggtgctggcc ccctcggagg agagcgagaa     360
gtacatcctg accctgcaga cggtgcactt cacttctgaa gctgtggagt tgcaggatat     420
```

```
gagcttgctg agcatacagc agcaagaagg ggtgcaggtg gtggtgcaac agcctggccc      480
tgggttgctg tggcttgagg aagggccccg gcagagcctg cagcagtgtg tggccattag      540
tatccagcaa gagctgtact ccccgcaaga gatggaggtt ttgcagttcc acgtctaga       600 ggagaatgtg atggtggcca gtgaagacag taagttagcg gtgagcctgg ctgaaactgc      660
tggactgatc aagctcgagg aagagcagga gaagaaccag ttattggctg aaagaacaaa      720
ggagcagctc ttttttgtgg aaacaatgtc aggagatgaa agaagtgacg aaattgttct      780
cacagtttca aattcaaatg tggaagaaca agaggatcaa cctacagctg gtcaagcaga      840
tgctgaaaag gccaaatcta caaaaaatca agaaagaca aagggagcaa aaggaacctt       900
ccactgtgat gtctgcatgt tcacctcttc tagaatgtca agttttaatc gtcatatgaa      960
aactcacacc agtgagaagc ctcacctgtg tcacctctgc ctgaaaacct tccgtacggt     1020
cactctgctg cggaaccatg ttaacaccca cacaggaacc aggccctaca agtgtaacga     1080
ctgcaacatg gcatttgtca ccagtggaga actcgtccga cacaggcgct ataaacatac     1140
tcatgagaaa ccctttaaat gttccatgtg caagtatgcc agtgtggagg caagtaaatt     1200
gaagcgccat gtccgatccc acactgggga gcgcccctt cagtgttgcc agtgcagcta     1260
tgccagcaga gatacctaca agctgaaacg ccacatgaga acgcactcag gtgagaagcc     1320
ttacgaatgc cacatctgcc acaccgctt cacccagagc gggaccatga aaatacatat     1380
tctgcagaaa cacggcgaaa atgtccccaa ataccagtgt ccccattgtg ccaccatcat     1440
tgcacggaaa agcgacctac gtgtgcatat gcgcaacttg catgcttaca gcgctgcaga     1500
gctgaaatgc cgctactgtt ctgctgtctt ccatgaacgc tatgccctca ttcagcacca     1560
gaaaactcat aagaatgaga gaggttcaa gtgcaaacac tgcagttatg cctgcaagca     1620
ggaacgtcat atgaccgctc acattcgtac ccacactgga gagaaaccat tcacctgcct     1680
ttcttgcaat aaatgttttcc gacagaagca acttctaaac gctcacttca ggaaatacca     1740
cgatgcaaat ttcatcccga ctgtttacaa atgctccaag tgtggcaaag gcttttcccg     1800
ctggattaac ctgcacagac attcggagaa gtgtggatca ggggaagcaa agtcggctgc     1860
ttcaggaaag ggaagaagaa caagaaagag gaagcagacc atcctgaagg aagccacaaa     1920
gggtcagaag gaagctgcga agggatgaa ggaagccgcg aacggagacg aagctgctgc      1980
tgaggaggct tccaccacga agggagaaca gttcccagga gagatgttc ctgtcgcctg      2040 cagagaaacc acagccagag tcaaagagga agtggatgaa ggcgtgacct gtgaaatgct     2100
cctcaacacg atggataagt gagagggatt cgggttgcgt gttcactgcc cccaattcct     2160
aaagcaagtt agaagttttt agcatttaag gtgtgaaatg ctcctcaaca cgatggataa     2220
gtgagagaga gtcaggttgc atgttcactg cccctaatc ctaaagcaag ttagaaattt      2280
ttagcatttt ctttgaaaca attaagttca tgacaatgga tgacacaagt ttgaggtagt     2340
gtctagaatt gttctcctgt ttgtagctgg atatttcaaa gaaacattgc aggtattta      2400 taaaagtttt aaaccttgaa tgagagggta acacctcaaa cctatggatt cattcacttg     2460
atattggcaa ggtggcccac aatgagtgag tagtgatttt tggatatttc aaaatagtct     2520
agaccagcta gtgcttccac agtcaaagct ggacatttt atgttgcatt atatacaccc       2580
atgatatttc taataatata tggttttaaa cattaaagac aaatgttttt atacaaatga     2640
attttctaca aaatttaaag ctaccataat gcttttaatt agttctaaat tcaaccaaaa     2700
aatgttttac tcttataaaa aggaaaactg agtaggaaat gaaatactag attagactag     2760
```

-continued

```
aaaataagga ataaatcgat tttactttgg tataggagca aggttcacct ttagattttt      2820
gtattctctt ttaattatgc tccttggcag gtatgaaatt gccctggtta cattccatta      2880
ttgcttatta gtatttcact ccataaccct tttttctgct aaaactactc tttttatatt      2940
tgtaaaataa ttggcagagt gagaagaaac ataaaatcag ataaggcaaa tgtgtacctg      3000
taaggaattt gtacttttc ataatgccca gtgattagtg agtatttccc ttttgccagt       3060
tgacaagatt tttccaccct cgagcagcgt gagagatgcc tctttaacac ttgaaattca      3120
tttctatctg gatacagagg cagatttttc ttcattgctt agttgagcag tttgttttgc      3180
tgccaacctg tctccacccc tgtatttcaa gatcattgat aagccctaaa ttcaaattct      3240
taagatatgg acctttat gaaaatatca caagttcaga atccctatac aatgtgaata        3300
tgtggaaata atttcccagc aggaagagca ttatattctc tttgtaccag caaattaatt      3360
taactcaact cacatgagat ttaaattctg tgggctgtag tatgccatca ttgtgactga      3420
atttgtgcaa tggtttctta attttttttac tgttatttaa agatgtttta cataattcaa     3480
taaaatgaaa tgacttaaaa ttgcaaaaaa aaaaaaaaaa aaaaaaaaa aaaaaaaaa        3540 a                                                                     3541
```

<210> SEQ ID NO 2
<211> LENGTH: 663
<212> TYPE: PRT
<213> ORGANISM: Homo sapiens

<400> SEQUENCE: 2

```
Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
            20                  25                  30

Asp Gly Val Cys Arg Glu Lys Asp His Arg Ser Pro Ser Glu Leu Glu
        35                  40                  45

Ala Glu Arg Thr Ser Gly Ala Phe Gln Asp Ser Val Leu Glu Glu Glu
    50                  55                  60

Val Glu Leu Val Leu Ala Pro Ser Glu Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Gln Glu Gly Val Gln Val Val Val
            100                 105                 110

Gln Gln Pro Gly Pro Gly Leu Leu Trp Leu Glu Glu Gly Pro Arg Gln
        115                 120                 125

Ser Leu Gln Gln Cys Val Ala Ile Ser Ile Gln Gln Glu Leu Tyr Ser
    130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Ala Gly Leu Ile Lys Leu Glu Glu Gln Glu Lys Asn Gln Leu Leu
            180                 185                 190

Ala Glu Arg Thr Lys Glu Gln Leu Phe Phe Val Glu Thr Met Ser Gly
        195                 200                 205

Asp Glu Arg Ser Asp Glu Ile Val Leu Thr Val Ser Asn Ser Asn Val
    210                 215                 220

Glu Glu Gln Glu Asp Gln Pro Thr Ala Gly Gln Ala Asp Ala Glu Lys
```

```
                225                 230                 235                 240
Ala Lys Ser Thr Lys Asn Gln Arg Lys Thr Lys Gly Ala Lys Gly Thr
                245                 250                 255

Phe His Cys Asp Val Cys Met Phe Thr Ser Ser Arg Met Ser Ser Phe
                260                 265                 270

Asn Arg His Met Lys Thr His Thr Ser Glu Lys Pro His Leu Cys His
                275                 280                 285

Leu Cys Leu Lys Thr Phe Arg Thr Val Thr Leu Leu Arg Asn His Val
                290                 295                 300

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Val
                340                 345                 350

Glu Ala Ser Lys Leu Lys Arg His Val Arg Ser His Thr Gly Glu Arg
                355                 360                 365

Pro Phe Gln Cys Gln Cys Ser Tyr Ala Ser Arg Asp Thr Tyr Lys
                370                 375                 380

Leu Lys Arg His Met Arg Thr His Ser Gly Glu Lys Pro Tyr Glu Cys
385                 390                 395                 400

His Ile Cys His Thr Arg Phe Thr Gln Ser Gly Thr Met Lys Ile His
                405                 410                 415

Ile Leu Gln Lys His Gly Glu Asn Val Pro Lys Tyr Gln Cys Pro His
                420                 425                 430

Cys Ala Thr Ile Ile Ala Arg Lys Ser Asp Leu Arg Val His Met Arg
                435                 440                 445

Asn Leu His Ala Tyr Ser Ala Ala Glu Leu Lys Cys Arg Tyr Cys Ser
                450                 455                 460

Ala Val Phe His Glu Arg Tyr Ala Leu Ile Gln His Gln Lys Thr His
465                 470                 475                 480

Lys Asn Glu Lys Arg Phe Lys Cys Lys His Cys Ser Tyr Ala Cys Lys
                485                 490                 495

Gln Glu Arg His Met Thr Ala His Ile Arg Thr His Thr Gly Glu Lys
                500                 505                 510

Pro Phe Thr Cys Leu Ser Cys Asn Lys Cys Phe Arg Gln Lys Gln Leu
                515                 520                 525

Leu Asn Ala His Phe Arg Lys Tyr His Asp Ala Asn Phe Ile Pro Thr
                530                 535                 540

Val Tyr Lys Cys Ser Lys Cys Gly Lys Gly Phe Ser Arg Trp Ile Asn
545                 550                 555                 560

Leu His Arg His Ser Glu Lys Cys Gly Ser Gly Glu Ala Lys Ser Ala
                565                 570                 575

Ala Ser Gly Lys Gly Arg Arg Thr Arg Lys Arg Gln Thr Ile Leu
                580                 585                 590

Lys Glu Ala Thr Lys Gly Gln Lys Glu Ala Ala Lys Gly Trp Lys Glu
                595                 600                 605

Ala Ala Asn Gly Asp Glu Ala Ala Glu Glu Ala Ser Thr Thr Lys
                610                 615                 620

Gly Glu Gln Phe Pro Gly Glu Met Phe Pro Val Ala Cys Arg Glu Thr
625                 630                 635                 640

Thr Ala Arg Val Lys Glu Glu Val Asp Glu Gly Val Thr Cys Glu Met
                645                 650                 655
```

Leu Leu Asn Thr Met Asp Lys
        660

<210> SEQ ID NO 3
<211> LENGTH: 2337
<212> TYPE: DNA
<213> ORGANISM: Mouse

<400> SEQUENCE: 3

| | | | | | |
|---|---|---|---|---|---|
| ccattttgtg | cacttgatc | aaagcccatg | tctactaggc | cccagcacct | ctgcacccca | 60 |
| taaagattgc | acgctctttt | tccatcaggg | gtcgtcacca | tggctgccgc | tgaggtccct | 120 |
| gtcccttctg | ggtacttcac | ccagatcaaa | gagcagaagt | tgaagcctgg | agacctagag | 180 |
| gaggagaaag | aggaggacgg | ggtacaaaga | gtggaagccc | aggagggagt | tgtcaaggag | 240 |
| gtggaggccg | agaacagttg | cctgcttctg | gaggccaggg | cccggtggga | gagcgacagg | 300 |
| cggatcctga | ccctgcaaac | ggtgcacctg | gagtcccagg | atgtgcacct | acaggggctg | 360 |
| ggatggctga | gcgtgccaca | ctctgaggag | cttcaggga | cggtaccaga | ggcggaaggc | 420 |
| atactgcagt | tgccatccgt | gctgtggctc | gacccagagc | cccagctcag | ccttcagcat | 480 |
| tgcgtgacgg | tcagcatccc | ggaagagctg | tacccaccag | aggagctgca | gcggatacat | 540 |
| tttcacctgc | tgagagagaa | tgtgctaatg | gccgaggaga | acccagagtt | aacaccagac | 600 |
| ttggacgaaa | gcacagccct | gaaaaagccc | gaagaagatg | aaaaggacca | gctcccgccc | 660 |
| caggagaga | cagacaagag | agaagagagg | ttgctccttc | tggaaatgaa | accaaaagag | 720 |
| ggaaaagacg | acgaaattgt | cctgaccatt | tcccatctaa | gcctcgaaga | acagcaagat | 780 |
| ccaccagcgg | ccaatcagac | aagtgtgccg | ggagccaaag | ccgcaaaacc | aaaacggcgg | 840 |
| aggcagacca | agggaaagcc | tcagagcttt | cagtgtgaca | cctgcccgtt | cacttcctcc | 900 |
| aagctctcaa | ctttcaatcg | tcacatcaaa | attcacagca | atgagaggcc | acacctgtgt | 960 |
| cacctgtgcc | tgaaggcctt | ccggactgtc | actcttctta | ggaaccatgt | gaacacccac | 1020 |
| acaggaacca | ggccccacaa | gtgcagggac | tgcgacatgg | cgtttgtcac | cagcggagaa | 1080 |
| ctcgtccggc | acaggcgtta | caaacacact | tatgagaagc | ccttcaagtg | ctccctgtgc | 1140 |
| aagtacgcca | gcgtcgaggc | aagcaagatg | aagcgtcaca | tccgctcaca | cacgggtgag | 1200 |
| cgtcccttcc | agtgttgcca | gtgtgcttat | gccagcaggg | actcctacaa | gctgaagcgc | 1260 |
| cacatgagga | cacactcagg | tgagaagccg | tatgaatgtc | ccacctgtca | cgtccggttc | 1320 |
| acccagagcg | ggaccatgaa | aatccatata | gcacagaagc | acgagagaa | tgtgcccaaa | 1380 |
| tacgagtgtc | cccactgtgc | caccatcatc | gcgaggaaga | gcgacctgcg | tgtccatctg | 1440 |
| cgtaacctgc | acagccagag | cccggaggag | atgaagtgcc | gatactgtcc | cgctggcttc | 1500 |
| catgagcgct | atgccctcat | tcagcaccag | aggacccaca | agaacgagaa | gaagttcaag | 1560 |
| tgcaagcagt | gcgattacgc | gtgcaagcag | gagcgatgct | tgaaggcgca | catgcgcatg | 1620 |
| cacacaggag | agaagccctt | ctcctgcctg | gcctgcaaca | agcacttccg | acagaagcag | 1680 |
| ctactgaccg | tgcacctgag | gaagtaccat | gacccgaact | tcgtcccaa | tctgcacctg | 1740 |
| tgcctcaagt | gtgataaacg | tttctcccgc | tggagtaacc | tgcagagaca | cagaaagaag | 1800 |
| tgtgaccccgg | agcatgagac | gttagccccc | aacaaggaca | ggagaccagt | gacaaggaca | 1860 |
| caggcctcgg | agggagaagc | aggacacaag | gaagggagc | ctcagtgccc | tggggagcag | 1920 |
| gctctgggcc | accaaggaga | agcagcgggg | agccagagcc | cagaccacgg | ccttacctgc | 1980 |
| gagatgatct | ttaacatgat | ggataagtga | tggataagtg | agcagtcgtg | cctctccgtg | 2040 |

-continued

```
cagtggcctc tgggggaaga aaccagttag aaataagttc ccagacacag cacagtgttc    2100
tcagagtttg agatagtgtg tagaaatgtt tgagagaagg ggaaaaaaac cctgcagcta    2160
tttccaaaga cttgagtcag agctcgaagt gaaggtgcac atatctgggc cctagcaggt    2220
gcccagaatg agtcagggac agattctagg tgatacttat gtccacgggg gctcagacca    2280
gttaacgcct tggtggtcag agcagaaaat ttttgagtt gttgtaccca ccctcaa      2337
```

```
<210> SEQ ID NO 4
<211> LENGTH: 636
<212> TYPE: PRT
<213> ORGANISM: Mouse

<400> SEQUENCE: 4
```

Met Ala Ala Glu Val Pro Val Pro Ser Gly Tyr Phe Thr Gln Ile
1               5                   10                  15

Lys Glu Gln Lys Leu Lys Pro Gly Asp Leu Glu Glu Lys Glu Glu
                20                  25                  30

Asp Gly Val Gln Arg Val Glu Ala Gln Glu Gly Val Val Lys Glu Val
            35                  40                  45

Glu Ala Glu Asn Ser Cys Leu Leu Glu Ala Arg Ala Pro Val Glu
50                  55                  60

Ser Asp Arg Arg Ile Leu Thr Leu Gln Thr Val His Leu Glu Ser Gln
65                  70                  75                  80

Asp Val His Leu Gln Gly Leu Gly Trp Leu Ser Val Pro His Ser Glu
                85                  90                  95

Glu Leu Ser Gly Thr Val Pro Glu Ala Glu Gly Ile Leu Gln Leu Pro
            100                 105                 110

Ser Val Leu Trp Leu Asp Pro Glu Pro Gln Leu Ser Leu Gln His Cys
        115                 120                 125

Val Thr Val Ser Ile Pro Glu Glu Leu Tyr Pro Pro Glu Glu Leu Gln
130                 135                 140

Arg Ile His Phe His Leu Leu Arg Glu Asn Val Leu Met Ala Glu Glu
145                 150                 155                 160

Asn Pro Glu Leu Thr Pro Asp Leu Asp Glu Ser Thr Ala Leu Lys Lys
                165                 170                 175

Pro Glu Glu Asp Glu Lys Asp Gln Leu Pro Pro Gln Gly Glu Thr Asp
            180                 185                 190

Lys Arg Glu Glu Arg Leu Leu Leu Leu Glu Met Lys Pro Lys Glu Gly
        195                 200                 205

Lys Asp Asp Glu Ile Val Leu Thr Ile Ser His Leu Ser Leu Glu Glu
210                 215                 220

Gln Gln Asp Pro Pro Ala Ala Asn Gln Thr Ser Val Pro Gly Ala Lys
225                 230                 235                 240

Ala Ala Lys Pro Lys Arg Arg Gln Thr Lys Gly Lys Pro Gln Ser
                245                 250                 255

Phe Gln Cys Asp Thr Cys Pro Phe Thr Ser Ser Lys Leu Ser Thr Phe
            260                 265                 270

Asn Arg His Ile Lys Ile His Ser Asn Glu Arg Pro His Leu Cys His
        275                 280                 285

Leu Cys Leu Lys Ala Phe Arg Thr Val Thr Leu Leu Arg Asn His Val
    290                 295                 300

Asn Thr His Thr Gly Thr Arg Pro His Lys Cys Arg Asp Cys Asp Met
305                 310                 315                 320

-continued

```
Ala Phe Val Thr Ser Gly Glu Leu Val Arg His Arg Tyr Lys His
            325                 330                 335

Thr Tyr Glu Lys Pro Phe Lys Cys Ser Leu Cys Lys Tyr Ala Ser Val
            340                 345                 350

Glu Ala Ser Lys Met Lys Arg His Ile Arg Ser His Thr Gly Glu Arg
            355                 360                 365

Pro Phe Gln Cys Cys Gln Cys Ala Tyr Ala Ser Arg Asp Ser Tyr Lys
            370                 375                 380

Leu Lys Arg His Met Arg Thr His Ser Gly Glu Lys Pro Tyr Glu Cys
385                 390                 395                 400

Pro Thr Cys His Val Arg Phe Thr Gln Ser Gly Thr Met Lys Ile His
                405                 410                 415

Ile Ala Gln Lys His Gly Glu Asn Val Pro Lys Tyr Glu Cys Pro His
            420                 425                 430

Cys Ala Thr Ile Ile Ala Arg Lys Ser Asp Leu Arg Val His Leu Arg
            435                 440                 445

Asn Leu His Ser Gln Ser Pro Glu Glu Met Lys Cys Arg Tyr Cys Pro
            450                 455                 460

Ala Gly Phe His Glu Arg Tyr Ala Leu Ile Gln His Gln Arg Thr His
465                 470                 475                 480

Lys Asn Glu Lys Lys Phe Lys Cys Lys Gln Cys Asp Tyr Ala Cys Lys
                485                 490                 495

Gln Glu Arg Cys Leu Lys Ala His Met Arg Met His Thr Gly Glu Lys
            500                 505                 510

Pro Phe Ser Cys Leu Ala Cys Asn Lys His Phe Arg Gln Lys Gln Leu
            515                 520                 525

Leu Thr Val His Leu Arg Lys Tyr His Asp Pro Asn Phe Val Pro Asn
            530                 535                 540

Leu His Leu Cys Leu Lys Cys Asp Lys Arg Phe Ser Arg Trp Ser Asn
545                 550                 555                 560

Leu Gln Arg His Arg Lys Cys Asp Pro Glu His Glu Thr Leu Ala
                565                 570                 575

Pro Asn Lys Asp Arg Arg Pro Val Thr Arg Thr Gln Ala Ser Glu Gly
            580                 585                 590

Glu Ala Gly His Lys Glu Gly Glu Pro Gln Cys Pro Gly Glu Gln Ala
            595                 600                 605

Leu Gly His Gln Gly Glu Ala Ala Gly Ser Gln Ser Pro Asp His Gly
            610                 615                 620

Leu Thr Cys Glu Met Ile Phe Asn Met Met Asp Lys
625                 630                 635

<210> SEQ ID NO 5
<211> LENGTH: 44
<212> TYPE: DNA
<213> ORGANISM: Artificial
<220> FEATURE:
<223> OTHER INFORMATION: Synthetic

<400> SEQUENCE: 5
ctagagcccc tcggccgccc cctcgcggcg cgccctcccc gctt            44

<210> SEQ ID NO 6
<211> LENGTH: 22
<212> TYPE: DNA
<213> ORGANISM: Artificial
<220> FEATURE:
<223> OTHER INFORMATION: Synthetic
```

-continued

<400> SEQUENCE: 6
gagcctgtgg agcgattaaa cc                                             22

<210> SEQ ID NO 7
<211> LENGTH: 15
<212> TYPE: DNA
<213> ORGANISM: Artificial
<220> FEATURE:
<223> OTHER INFORMATION: Synthetic

<400> SEQUENCE: 7
ccgccgccgc tccac                                                     15

<210> SEQ ID NO 8
<211> LENGTH: 20
<212> TYPE: DNA
<213> ORGANISM: Artificial
<220> FEATURE:
<223> OTHER INFORMATION: Synthetic

<400> SEQUENCE: 8
cttctttggc ggcagcggcg                                                20

<210> SEQ ID NO 9
<211> LENGTH: 17
<212> TYPE: DNA
<213> ORGANISM: Artificial
<220> FEATURE:
<223> OTHER INFORMATION: Synthetic

<400> SEQUENCE: 9
cgcgccacac cccccgc                                                   17

<210> SEQ ID NO 10
<211> LENGTH: 14
<212> TYPE: DNA
<213> ORGANISM: Artificial
<220> FEATURE:
<223> OTHER INFORMATION: Synthetic

<400> SEQUENCE: 10
ccccagaacc agac                                                      14

<210> SEQ ID NO 11
<211> LENGTH: 17
<212> TYPE: DNA
<213> ORGANISM: Artificial
<220> FEATURE:
<223> OTHER INFORMATION: Synthetic

<400> SEQUENCE: 11
acttcagtct tcatctg                                                   17

<210> SEQ ID NO 12
<211> LENGTH: 20
<212> TYPE: DNA
<213> ORGANISM: Artificial
<220> FEATURE:
<223> OTHER INFORMATION: Synthetic

<400> SEQUENCE: 12
tgtgagcttt gcagttacac                                                20

<210> SEQ ID NO 13

-continued

```
<211> LENGTH: 18
<212> TYPE: DNA
<213> ORGANISM: Artificial
<220> FEATURE:
<223> OTHER INFORMATION: Synthetic

<400> SEQUENCE: 13
actgttctga atgccctg                                                 18

<210> SEQ ID NO 14
<211> LENGTH: 16
<212> TYPE: DNA
<213> ORGANISM: Artificial
<220> FEATURE:
<223> OTHER INFORMATION: Synthetic

<400> SEQUENCE: 14
cggcgttcaa atttgg                                                   16

<210> SEQ ID NO 15
<211> LENGTH: 20
<212> TYPE: DNA
<213> ORGANISM: Artificial
<220> FEATURE:
<223> OTHER INFORMATION: Synthetic

<400> SEQUENCE: 15
cgagtacctg tgtgtgtgtt                                               20

<210> SEQ ID NO 16
<211> LENGTH: 15
<212> TYPE: DNA
<213> ORGANISM: Artificial
<220> FEATURE:
<223> OTHER INFORMATION: Synthetic

<400> SEQUENCE: 16
gtgcccagac tgcga                                                    15

<210> SEQ ID NO 17
<211> LENGTH: 17
<212> TYPE: DNA
<213> ORGANISM: Artificial
<220> FEATURE:
<223> OTHER INFORMATION: Synthetic

<400> SEQUENCE: 17
aatcgcacat ggaacac                                                  17

<210> SEQ ID NO 18
<211> LENGTH: 17
<212> TYPE: DNA
<213> ORGANISM: Artificial
<220> FEATURE:
<223> OTHER INFORMATION: Synthetic

<400> SEQUENCE: 18
ttcaagtgtt ccatgtg                                                  17

<210> SEQ ID NO 19
<211> LENGTH: 18
<212> TYPE: DNA
<213> ORGANISM: Artificial
<220> FEATURE:
<223> OTHER INFORMATION: Synthetic

<400> SEQUENCE: 19
```
ctgctggcat aactgcac                                                        18

<210> SEQ ID NO 20
<211> LENGTH: 19
<212> TYPE: DNA
<213> ORGANISM: Artificial
<220> FEATURE:
<223> OTHER INFORMATION: Synthetic

<400> SEQUENCE: 20
cacatacaag ctgaaaagg                                                       19

<210> SEQ ID NO 21
<211> LENGTH: 18
<212> TYPE: DNA
<213> ORGANISM: Artificial
<220> FEATURE:
<223> OTHER INFORMATION: Synthetic

<400> SEQUENCE: 21
gcatcttcat ggtaccac                                                        18

<210> SEQ ID NO 22
<211> LENGTH: 19
<212> TYPE: DNA
<213> ORGANISM: Artificial
<220> FEATURE:
<223> OTHER INFORMATION: Synthetic

<400> SEQUENCE: 22
gtcatagccc gaaaaagtg                                                       19

<210> SEQ ID NO 23
<211> LENGTH: 17
<212> TYPE: DNA
<213> ORGANISM: Artificial
<220> FEATURE:
<223> OTHER INFORMATION: Synthetic

<400> SEQUENCE: 23
cgctcatgaa acacagc                                                         17

<210> SEQ ID NO 24
<211> LENGTH: 18
<212> TYPE: DNA
<213> ORGANISM: Artificial
<220> FEATURE:
<223> OTHER INFORMATION: Synthetic

<400> SEQUENCE: 24
gtgtgaccag tgtgatta                                                        18

<210> SEQ ID NO 25
<211> LENGTH: 17
<212> TYPE: DNA
<213> ORGANISM: Artificial
<220> FEATURE:
<223> OTHER INFORMATION: Synthetic

<400> SEQUENCE: 25
ttctggcgga aggtctt                                                         17

<210> SEQ ID NO 26
<211> LENGTH: 17
<212> TYPE: DNA

<213> ORGANISM: Artificial
<220> FEATURE:
<223> OTHER INFORMATION: Synthetic

<400> SEQUENCE: 26
caagcgctat cacgacc                                                  17

<210> SEQ ID NO 27
<211> LENGTH: 17
<212> TYPE: DNA
<213> ORGANISM: Artificial
<220> FEATURE:
<223> OTHER INFORMATION: Synthetic

<400> SEQUENCE: 27
tctgcatgtc ttgccat                                                  17

<210> SEQ ID NO 28
<211> LENGTH: 20
<212> TYPE: DNA
<213> ORGANISM: Artificial
<220> FEATURE:
<223> OTHER INFORMATION: Synthetic

<400> SEQUENCE: 28
tcctctgaca gtgaaaatgc                                               20

<210> SEQ ID NO 29
<211> LENGTH: 18
<212> TYPE: DNA
<213> ORGANISM: Artificial
<220> FEATURE:
<223> OTHER INFORMATION: Synthetic

<400> SEQUENCE: 29
cacaggctga ggctctgg                                                 18

<210> SEQ ID NO 30
<211> LENGTH: 19
<212> TYPE: DNA
<213> ORGANISM: Artificial
<220> FEATURE:
<223> OTHER INFORMATION: Synthetic

<400> SEQUENCE: 30
cagaatacag gtgcaattg                                                19

<210> SEQ ID NO 31
<211> LENGTH: 18
<212> TYPE: DNA
<213> ORGANISM: Artificial
<220> FEATURE:
<223> OTHER INFORMATION: Synthetic

<400> SEQUENCE: 31
caccggtcca tcatgctg                                                 18

<210> SEQ ID NO 32
<211> LENGTH: 27
<212> TYPE: DNA
<213> ORGANISM: Artificial
<220> FEATURE:
<223> OTHER INFORMATION: Synthetic

<400> SEQUENCE: 32
gccagtgtgg aggcaagtaa attgaag                                       27

<210> SEQ ID NO 33
<211> LENGTH: 29
<212> TYPE: DNA
<213> ORGANISM: Artificial
<220> FEATURE:
<223> OTHER INFORMATION: Synthetic

<400> SEQUENCE: 33
cactggcaac actgaaaggg gcgctcccc                              29

<210> SEQ ID NO 34
<211> LENGTH: 22
<212> TYPE: DNA
<213> ORGANISM: Artificial
<220> FEATURE:
<223> OTHER INFORMATION: Synthetic

<400> SEQUENCE: 34
tcgtcatatg aaaactcaca cc                                     22

<210> SEQ ID NO 35
<211> LENGTH: 19
<212> TYPE: DNA
<213> ORGANISM: Artificial
<220> FEATURE:
<223> OTHER INFORMATION: Synthetic

<400> SEQUENCE: 35
gacgagttct ccactggtg                                         19

<210> SEQ ID NO 36
<211> LENGTH: 20
<212> TYPE: DNA
<213> ORGANISM: Artificial
<220> FEATURE:
<223> OTHER INFORMATION: Synthetic

<400> SEQUENCE: 36
aacatactca tgagaaaccc                                        20

<210> SEQ ID NO 37
<211> LENGTH: 18
<212> TYPE: DNA
<213> ORGANISM: Artificial
<220> FEATURE:
<223> OTHER INFORMATION: Synthetic

<400> SEQUENCE: 37
gagtgcgttc tcatgtgg                                          18

<210> SEQ ID NO 38
<211> LENGTH: 18
<212> TYPE: DNA
<213> ORGANISM: Artificial
<220> FEATURE:
<223> OTHER INFORMATION: Synthetic

<400> SEQUENCE: 38
gagcgcccct ttcagtgt                                          18

<210> SEQ ID NO 39
<211> LENGTH: 15
<212> TYPE: DNA
<213> ORGANISM: Artificial
<220> FEATURE:

<223> OTHER INFORMATION: Synthetic

<400> SEQUENCE: 39
gcacaatggg gacac                                                    15

<210> SEQ ID NO 40
<211> LENGTH: 21
<212> TYPE: DNA
<213> ORGANISM: Artificial
<220> FEATURE:
<223> OTHER INFORMATION: Synthetic

<400> SEQUENCE: 40
acccagagcg ggaccatgaa a                                             21

<210> SEQ ID NO 41
<211> LENGTH: 19
<212> TYPE: DNA
<213> ORGANISM: Artificial
<220> FEATURE:
<223> OTHER INFORMATION: Synthetic

<400> SEQUENCE: 41
gacagcagaa cagtagcgg                                                19

<210> SEQ ID NO 42
<211> LENGTH: 18
<212> TYPE: DNA
<213> ORGANISM: Artificial
<220> FEATURE:
<223> OTHER INFORMATION: Synthetic

<400> SEQUENCE: 42
cataagaatg agaagagg                                                 18

<210> SEQ ID NO 43
<211> LENGTH: 19
<212> TYPE: DNA
<213> ORGANISM: Artificial
<220> FEATURE:
<223> OTHER INFORMATION: Synthetic

<400> SEQUENCE: 43
aagttgcttc tgtcggaaa                                                19

<210> SEQ ID NO 44
<211> LENGTH: 21
<212> TYPE: DNA
<213> ORGANISM: Artificial
<220> FEATURE:
<223> OTHER INFORMATION: Synthetic

<400> SEQUENCE: 44
ttgtgcagtt atgccagcag g                                             21

<210> SEQ ID NO 45
<211> LENGTH: 22
<212> TYPE: DNA
<213> ORGANISM: Artificial
<220> FEATURE:
<223> OTHER INFORMATION: Synthetic

<400> SEQUENCE: 45
gtgcttctgt aaaatgtgca tc                                            22

```
<210> SEQ ID NO 46
<211> LENGTH: 27
<212> TYPE: DNA
<213> ORGANISM: Artificial
<220> FEATURE:
<223> OTHER INFORMATION: Synthetic

<400> SEQUENCE: 46
caggccctac aagtgtaacg actgcaa                                          27

<210> SEQ ID NO 47
<211> LENGTH: 27
<212> TYPE: DNA
<213> ORGANISM: Artificial
<220> FEATURE:
<223> OTHER INFORMATION: Synthetic

<400> SEQUENCE: 47
gcattcgtaa ggcttctcac ctgagtg                                          27

<210> SEQ ID NO 48
<211> LENGTH: 32
<212> TYPE: DNA
<213> ORGANISM: Artificial
<220> FEATURE:
<223> OTHER INFORMATION: Synthetic

<400> SEQUENCE: 48
gagagacaga caagagagaa gagaggttgc tc                                    32

<210> SEQ ID NO 49
<211> LENGTH: 32
<212> TYPE: DNA
<213> ORGANISM: Artificial
<220> FEATURE:
<223> OTHER INFORMATION: Synthetic

<400> SEQUENCE: 49
cctgtgtggg tgttcacatg gttcctaaga ag                                    32
```